(12) United States Patent
Abtab et al.

(10) Patent No.: US 11,701,637 B2
(45) Date of Patent: Jul. 18, 2023

(54) CHROMIUM-BASED METAL-ORGANIC FRAMEWORKS FOR WATER ADSORPTION-RELATED APPLICATIONS AND GAS STORAGE

(71) Applicant: King Abdullah University of Science and Technology, Thuwal (SA)

(72) Inventors: Sk Md Towsif Abtab, Thuwal (SA); Youssef Belmabkhout, Thuwal (SA); Prashant Bhatt, Thuwal (SA); Mohamed Eddaoudi, Thuwal (SA)

(73) Assignee: King Abdullah University of Science And Technology, Thuwal (SA)

( * ) Notice: Subject to any disclaimer, the term of this patent is extended or adjusted under 35 U.S.C. 154(b) by 241 days.

(21) Appl. No.: 16/642,525

(22) PCT Filed: Sep. 19, 2018

(86) PCT No.: PCT/IB2018/057215
§ 371 (c)(1),
(2) Date: Feb. 27, 2020

(87) PCT Pub. No.: WO2019/058276
PCT Pub. Date: Mar. 28, 2019

(65) Prior Publication Data
US 2021/0069672 A1    Mar. 11, 2021

Related U.S. Application Data

(60) Provisional application No. 62/677,427, filed on May 29, 2018, provisional application No. 62/560,344, filed on Sep. 19, 2017.

(51) Int. Cl.
*B01D 53/04* (2006.01)
*B01J 20/22* (2006.01)
(Continued)

(52) U.S. Cl.
CPC ............ *B01J 20/226* (2013.01); *B01D 53/02* (2013.01); *B01D 53/261* (2013.01); *B01D 53/28* (2013.01);
(Continued)

(58) Field of Classification Search
CPC ...... B01D 53/02; B01D 53/04; B01D 53/261; B01D 53/28; B01D 2253/204;
(Continued)

(56) References Cited

U.S. PATENT DOCUMENTS 8,262,775 B2 * 9/2012 Farha ..................... B01J 20/22
 95/139
2016/0088106 A1 3/2016 Wang et al.
(Continued)

FOREIGN PATENT DOCUMENTS

CN    106807329 A    6/2017
WO    2016088106 A1    6/2016

OTHER PUBLICATIONS

Akiyama, et al., "Effect of Functional Groups in MIL-101 on Water Sorption Behavior", Microporous and Mesoporous Materials, vol. 157, 2012, pp. 89-93.
(Continued)

*Primary Examiner* — Frank M Lawrence, Jr.
(74) *Attorney, Agent, or Firm* — Billion & Armitage

(57) ABSTRACT

Embodiments of the present disclosure describe a metal-organic framework (MOF) composition comprising a plurality of metal clusters, wherein the metal is chromium; and one or more tetratopic ligands; wherein the metal clusters and ligands associate to form a MOF with soc topology. A method of making a MOF comprising contacting a template MOF of formula Fe-soc-MOF and a reactant including chromium in a presence of dimethylformamide sufficient to replace Fe with Cr and form an exchanged MOF of formula
(Continued)

Cr-soc-MOF. A method of sorbing water vapor comprising exposing a Cr-soc-MOF to an environment; and sorbing water vapor using the Cr-soc-MOF.

12 Claims, 23 Drawing Sheets

(51) Int. Cl.
| | |
|---|---|
| B01D 53/02 | (2006.01) |
| B01D 53/26 | (2006.01) |
| B01D 53/28 | (2006.01) |
| B01J 20/30 | (2006.01) |
| B01J 20/34 | (2006.01) |
| C07C 63/331 | (2006.01) |
| C07F 11/00 | (2006.01) |
| C07F 15/02 | (2006.01) |

(52) U.S. Cl.
CPC ....... *B01J 20/3085* (2013.01); *B01J 20/3458* (2013.01); *C07C 63/331* (2013.01); *C07F 11/005* (2013.01); *C07F 15/025* (2013.01); *B01D 2253/204* (2013.01); *B01D 2257/80* (2013.01)

(58) Field of Classification Search
CPC . B01D 2257/80; B01J 20/226; B01J 20/3085; B01J 20/3458; C07C 63/331; C07F 11/005; C07F 15/025
USPC .............. 96/108; 95/117, 900, 902; 502/401
See application file for complete search history.

(56) References Cited

U.S. PATENT DOCUMENTS

2020/0282379 A1* 9/2020 Mulet .................... B01J 20/226
2021/0283574 A1* 9/2021 Yaghi .................... B01J 20/226

OTHER PUBLICATIONS

Akiyama, et al., "Highly Porous and Stable Coordination Polymers as Water Sorption Materials", Chemistry Letters, vol. 39, Mar. 6, 2010, pp. 360-361.
Alezi, et al., "MOF Crystal Chemistry Paving the Way to Gas Storage Needs: Aluminum-Based soc-MOF for CH4, O2, and CO2 Storage", Journal of the American Chemical Society, vol. 137, Sep. 14, 2015, pp. 13308-13318.
Burtch, et al., "Water Stability and Adsorption in Metal-Organic Frameworks", Chemical Reviews, vol. 114, Sep. 29, 2014, pp. 10575-10612.
Canivet, et al., "Structure-Property Relationships of Water Adsorption in Metal-Organic Frameworks", New Journal of Chemistry, vol. 38, Apr. 16, 2014, pp. 3102-3111.
Canivet, et al., "Water Adsorption in MOFs: Fundamentals and Applications", Chemical Society Reviews, vol. 43, May 29, 2014, pp. 5594-5617.
Ehrenmann, et al., "Water Adsorption Characteristics of MIL-101 for Heat-Transformation Applications of MOFs", European Journal of Inorganic Chemistry, vol. 2011, 2011, pp. 471-474.
Furukawa, et al., "Water Adsorption in Porous Metal-Organic Frameworks and Related Materials", Journal of the American Chemical Society, vol. 136, Mar. 3, 2014, pp. 4369-4381.
Henninger, et al., "MOFs as Adsorbents for Low Temperature Heating and Cooling Applications", Journal of the American Chemical Society, vol. 131, No. 8, 2009, pp. 2776-2777.
Henninger, et al., "MOFs for Use in Adsorption Heat Pump Processes", European Journal of Inorganic Chemistry, vol. 2012, 2012, pp. 2625-2634.
Ko, et al., "Tailoring the Water Adsorption Properties of MIL-101 Metal-Organic Frameworks by Partial Functionalization", Journal of Materials Chemistry A, vol. 3, 2015, pp. 2057-2064.
Liu, et al., "Assembly of Metal-Organic Frameworks (MOFs) Based on Indium-Trimer Building Blocks: A Porous MOF with soc Topology and High Hydrogen Storage", Angewandte Chemie International Edition, vol. 46, 2007, pp. 3278-3283.
Pang, et al., "Highly Monodisperse MIII-Based soc-MOFs (M=In and Ga) with Cubic and Truncated Cubic Morphologies", Journal of the American Chemical Society, vol. 134, 2012, 6 pages.
Search Report and Written Opinion for Application No. PCT/IB2018/057215 dated Jan. 2, 2019.
Abtab, et al., "Chem, 4", Jan. 11, 2018, 94-105.
Alezi, et al., "MOF Crystal Chemistry Paving the Way to Gas Storage Needs: Aluminum-Based soc-MOF for CH4, O2 and CO2 Storage", Journal of the American Chemical Society, 137, 2015, 13308-13318.
Ko, et al., "tailoring the water adsorption properties of MIL-101 metal-organic frameworks by partial functionalization+", Journal of Materials Chemistry A, 3, 2015, 2057-2064.
Ko, N. , et al., "Tailoring the water adsorption properties of MIL-101 metal-organic frameworks by partial functionalization", Journal of Materials Chemistry A ,vol. 3, No. 5, XP055535118,, Jan. 1, 2015, pp. 2057-2064.
Communication pursuant to Article 94(3) EPC Application No. 18783117.7 , dated Oct. 7, 2022, 9 Pages.
Non Final Office Action received for Chinese Patent Application No. 2018800646903, dated Jul. 14, 2022, 21 pages.
Alezi, D. , et al., "Reticular Chemistry at Its Best: Directed Assembly of Hexagonal Building Units into the Awaited Metal-Organic Framework with the Intricate Polybenzene Topology, pbz-MOF", Journal of the American Chemical Society vol. 138, No. 39, XP055706166, Sep. 24, 2016, pp. 12767-12770.
"Second Office Action Received for Chinese Application No. 2018800646903, dated Feb. 8, 2023", 12 Pages.

* cited by examiner

Fe-soc-MOF  Cr-soc-MOF oxo-centered trinuclear chromium (III) cluster

H₄TCPT

Cr-soc-MOF-1
$S_{BET} = 4549\ m^2/g$

CHROMIUM-BASED METAL-ORGANIC FRAMEWORKS FOR WATER ADSORPTION-RELATED APPLICATIONS AND GAS STORAGE

BACKGROUND

The development and deployment of energy-saving technologies offers great prospective to sustain and address the worldwide ever-increasing energy demand, and subsequently supports the foreseen lessening of the emitted carbon footprint. Credibly, the continuous globalization of a better quality of living imposes the consumption of excessive amounts of energy, as for the indoor air-conditioning in regions with extremely high or low temperatures, and for desalination of seawater in desert areas. Appositely, from indoor air conditioning perspective, adsorptive heat transformation (AHT) applications, provided optimal water vapor ($H_2O$) adsorbent is available, are considered to be highly energy-efficient and environmentally friendly technologies in contrast to the conventional compression-decompression systems. Perceptibly, air conditioning devices based on thermally driven adsorption heat pumps (AHP) or desiccant cooling systems (DCS) are considered to operate with a moderate electric power consumption. It is to be noted that working principle of both AHP and DCS systems are governed by the reversible exothermic adsorption and endothermic desorption of water in micro- or mesoporous solid materials. Coherently, porous materials with distinct water adsorption properties and remarkable water uptake are ideal for humidity control in confined and poorly ventilated space. It is important to note that very high (>65%) or very low (<25%) relative humidity levels are regarded to have adverse effects on human health and comfort level. Considerately, materials with the potential to adsorb large amount of water vapors at the undesired higher humidity and subsequently release it when the humidity level dropped below the recommended limit are well positioned to address the essentials for the commanded humidity control. Principally, the energy efficiency, working humidity range of AHP/DCS and the foreseen performance of humidity controller are directly correlated to the properties of the water vapor adsorbents. Logically, extensive research is devoted to the design, synthesis and development of new adsorbents whose water uptake capacity exceeds that of existing commercial materials (e.g. silica gels or zeolites) and offering a relatively milder regeneration conditions.

Metal-Organic Frameworks (MOFs), an emerging class of crystalline porous materials, are considered to offer great potential in addressing many enduring challenges pertaining to energy and environmental sustainability. Nevertheless, in spite of the attractive features of MOFs, stirred by their extraordinary porosity and a high degree of structural tunability and stability, the degradation of some earlier examples of highly porous MOFs in a water (moisture) containing environment hindered their readily industrial implementation. Remarkably, advances in MOF chemistry have permitted the deployment of several strategies for the synthesis of water stable MOFs, paving the way to water sorbent candidates for water adsorption related applications. From a qualitative point of view, the adsorption properties of MOFs are obviously quite diverse in terms of water uptake capacity and the associated relative pressure at which the pore filling occurs. Certainly, hydrolytically stable porous materials offering remarkable pore volumes are expected to exhibit large $H_2O$ adsorption capacity. Prominently, the quest for hydrolytically stable and recyclable MOFs with a superior total water uptake remains a focal point of intensive research in MOF chemistry.

In this context, Zirconium-based MOFs have attracted considerable attention due their exceptional chemical and thermal stability. Nonetheless, although numerous high surface area Zr-MOFs are chemically stable to water, their structure cannot sustain desorption of water as the said open framework collapses under the influence of capillary forces of desorbing water.

SUMMARY

In general, embodiments of the present disclosure describe chromium-based metal-organic framework compositions, methods of making chromium-based metal-organic frameworks, and methods of sorbing and/or desorbing water vapor using chromium-based metal-organic frameworks, and the like.

Accordingly, embodiments of the present disclosure describe methods of sorbing and/or desorbing water vapor comprising exposing a Cr-soc-MOF to an environment and sorbing water vapor using the Cr-soc-MOF.

Embodiments of the present disclosure describe metal-organic framework compositions comprising a plurality of metal clusters, wherein the metal is chromium, and one or more tetratopic ligands, wherein the metal clusters and ligands associate to form a metal-organic framework with soc topology.

Embodiments of the present disclosure describe methods of making metal-organic frameworks comprising contacting a template MOF of formula Fe-soc-MOF and a reactant including chromium in a presence of dimethylformamide sufficient to replace Fe with Cr and form an exchanged MOF of formula Cr-soc-MOF.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which.

DETAILED DESCRIPTION

Figure 1:
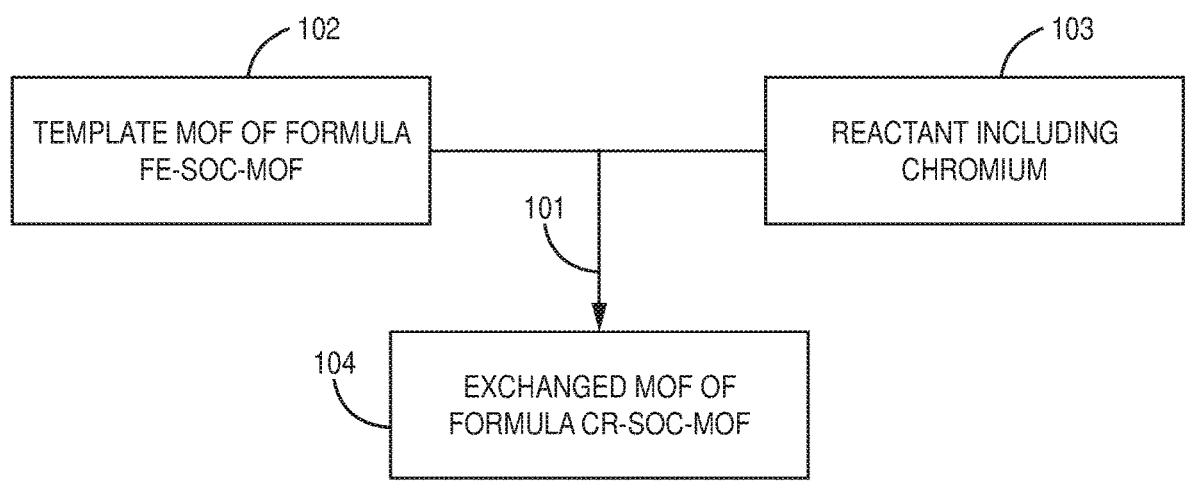
FIG. 1 is a flowchart of a method of making a metal-organic framework, according to one or more embodiments of the present disclosure.

The invention of the present disclosure relates to novel chromium-based metal-organic framework (MOF) compositions, methods of making chromium-based metal-organic framework compositions, and methods of using chromium-based metal-organic framework compositions. In particular, the invention of the present disclosure describes for the first time a chromium-based metal-organic framework with an underlying soc topology. For example, in an embodiment, the metal-organic frameworks may comprise a plurality of chromium clusters bridged by one or more tetratopic ligands that associate to form a chromium-based metal-organic framework with soc topology. In an exemplary embodiment, the metal-organic framework comprises a metal-organic framework of formula Cr-soc-MOF. In another exemplary embodiment, the metal-organic framework comprises Cr-soc-MOF-1.

While efforts to directly synthesize single-crystal quality Cr-soc-MOFs according to conventional methods are unsuccessful, the novel methods of the present disclosure were developed to obtain the crystalline chromium-based metal-organic frameworks described herein. The invention of the present disclosure thus also relates to methods of making chromium-based metal-organic frameworks via, for example, a post-synthetic approach. This approach includes post-synthetic metal cluster metathesis from a template MOF with a known structure to obtain isotructural and/or isoreticular chromium-based MOFs with soc topology. In particular, embodiments describe, among other things, a post-synthetic route based on transmetalation of a Fe-soc-MOF into the desired Cr-soc-MOF. For example, an embodiment describes single-crystal to single-crystal transformation of a $[Fe_3(\mu_3-O)(O_2C^-)_6]$ molecular building block (MBB) in Fe-soc-MOF-1 into [Cr$_3$($\mu_3$-O)(O$_2$C$^-$)$_6$] MBB to form isostructural Cr-soc-MOF-1 with near complete exchange of Fe for Cr.

The Cr-soc-MOFs of the present disclosure exhibit, among other things, a rare combination of extraordinarily high porosity, surface area, pore volume, high thermal and chemical stability, as well as unprecedented hydrolytic stability and exceptional water vapor adsorption capacity. For example, the Cr-soc-MOFs exhibit the highest water capacity reported to date and exceptionally high gas storage uptake. The working capacity of the Cr-soc-MOFs of the present disclosure is close to about 200 wt. % (e.g., about 1.95 g/g). No conventional materials (e.g., solid state materials), including MOFs, exhibit the same performance. This high uptake may be generated and the materials may be recycled by only applying a relative humidity or pressure driving force—e.g., without heating. Further, unlike conventional materials, the Cr-soc-MOFs maintain crystallinity and porosity upon exposure to moisture/water vapor. This rare combination of properties and characteristics of the Cr-soc-MOFs of the present disclosure confer unique water adsorption properties that make them particularly well-suited as adsorbents for water adsorption-related applications. The exceptional water adsorption features of Cr-soc-MOF-1 may be a direct result of combining the requisite structural characteristics in a single adsorbent, namely hydrolytic stability, ultra-high micropore volume, and the proper pore system (e.g., shape, size, and functionality), among other things. In this way, the invention of the present disclosure provides novel chromium-based metal-organic frameworks that are superior to and greatly outperform conventional adsorbents, especially with respect to water adsorption-related applications.

The Cr-soc-MOFs of the present disclosure outperform existing materials, including, but not limited to, other MOFs, carbons, and inorganic materials. In particular, the Cr-soc-MOFs of the present disclosure outperform existing materials at least in terms of total and working capacity, reversibility, and cyclic performance, among other things. For example, the hydrolytically stable and highly porous Cr-soc-MOF may capture an unprecedented twice its weight in water (e.g., about 200 wt. % of water). This is understood to be the highest value of water adsorbed at saturation among all MOFs, carbons, and inorganic materials. In addition, this exceptional water uptake may be maintained over more than 100 adsorption-desorption cycles. Also, the chromium-based metal-organic frameworks described herein may only require low to mild regeneration conditions, as adsorbed water may be desorbed (e.g., completely desorbed) simply by reducing relative humidity at about room temperature, suggesting an energy efficient and cost-effective recycling process.

Accordingly, the metal-organic frameworks may be used as adsorbents in a wide variety of applications, including, but not limited to, applications relating to water vapor control in enclosed and/or confined spaces, as well as dehumidification. The metal-organic frameworks may also be used and/or included in, among other things, adsorptive heat transformation applications, adsorption heat pumps (AHP), dessicant cooling systems (DCS), water desalination applications, etc.

Definitions

The terms recited below have been defined as described below. All other terms and phrases in this disclosure shall be construed according to their ordinary meaning as understood by one of skill in the art.

As used herein, "capturing" refers to the act of removing one or more chemical species from a bulk fluid composition (e.g., gas/vapor, liquid, and/or solid). For example, "capturing" may include, but is not limited to, interacting, bonding, diffusing, adsorbing, absorbing, reacting, and sieving, whether chemically, electronically, electrostatically, physically, or kinetically driven.

As used herein, "contacting" refers to the act of touching, making contact, or of bringing to close or immediate proximity, including at the cellular or molecular level, for example, to bring about a physiological reaction, a chemical reaction, or a physical change (e.g., in solution, in a reaction mixture, in vitro, or in vivo). Contacting may refer to bringing two or more components in proximity, such as physically, chemically, electrically, or some combination thereof. Mixing is an example of contacting.

As used herein, "contacting" may, in addition or in the alternative, refer to, among other things, feeding, flowing, passing, injecting, introducing, and/or providing the fluid composition (e.g., a feed gas).

As used herein, "exposing" refers to subjecting to conditions of an environment. For example, conditions of an environment may include, among other things, one or more of temperature, pressure, and chemical species present in the environment (e.g., water vapor as humidity or moisture). In addition or in the alternative, exposing refers to subjecting to objects present in an environment.

As used herein, "sorbing" refers to one or more of absorbing, adsorbing, and desorbing. Sorbing may include selective sorption, such as sorption of a single compound, subsequent sorption, such as sorption of a first compound and then a second compound, or simultaneous sorption, such as sorption of two or more compounds at about the same time.

Cr-Soc-MOF Compositions

Embodiments of the present disclosure describe a metal-organic framework composition. In particular, embodiments of the present disclosure describe a metal-organic framework composition comprising a plurality of metal clusters and one or more tetratopic ligands, wherein the metal clusters and ligands associate to form a metal-organic framework with soc topology. The metal clusters include a metal, such as chromium. The tetratopic ligands may include any tetratopic ligand represented by the chemical formula below:

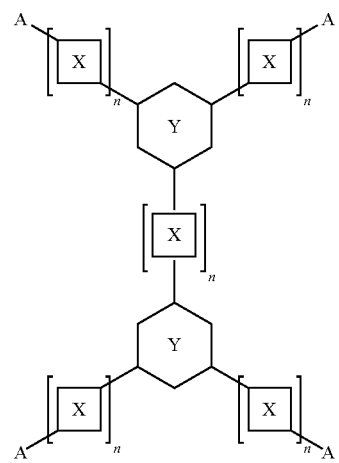

wherein each X can be independently selected from the group consisting of aryls, polyaryls, heteroaryls, and alkynes; wherein each Y can be independently selected from the group consisting of aryls and heteroaryls; wherein each A can be independently selected from the group consisting of COOH and azoles; wherein each n is at least 1. Examples of suitable azoles include, but are not limited to, tetrazole, triazole, and pyrazole. In an embodiment, the one or more ligands include 3,3",5,5"-tetrakis(4-carboxyphenyl)-p-terphenyl.

In an embodiment, the metal is chromium (e.g., Cr(III)) and the ligand is 3,3",5,5"-tetrakis(4-carboxyphenyl)-p-terphenyl. Accordingly, in an embodiment of the present disclosure, the metal-organic framework composition comprises a plurality of metal clusters, wherein the metal is chromium, and one or more tetratopic ligands, wherein the ligand is 3,3",5,5"-tetrakis(4-carboxyphenyl)-p-terphenyl, wherein the metal clusters and ligands associate to form a metal-organic framework with soc topology.

The Cr-soc-MOF may be crystalline. For example, in an embodiment, the Cr-soc-MOF is a monocrystalline or polycrystalline. In many embodiments, the Cr-soc-MOF is monocrystalline or a single-crystal MOF. The Cr-soc-MOF may be characterized as microporous, mesoporous, or a combination thereof. The chromium content of the Cr-soc-MOF may include up to about 98% chromium. In many embodiments, the Cr-soc-MOF contains at least about 90% chromium. In a preferred embodiment, the Cr-soc-MOF contains about 98% chromium. In other embodiments, the Cr-soc-MOF contains more than about 98% chromium or less than about 98% chromium. In many embodiments, an oxidation state of chromium is (+III). In some embodiments, the Cr-soc-MOF may further comprise one or more of a counterion and guest solvent. In an embodiment, the counterion is a counteranion. In an embodiment, the counterion is $Cl^-$.

Method of Making Cr-soc-MOFs

FIG. 1 is a flowchart of a method of making a metal-organic framework, according to one or more embodiments of the present disclosure. As shown in FIG. 1, the method comprises contacting 101 a template MOF of formula Fe-soc-MOF 102 and a reactant including chromium 103 in a presence of dimethylformamide (DMF) (not shown) sufficient to replace Fe with Cr and form an exchanged MOF of formula Cr-soc-MOF 104. Due to a relatively high inertness of Cr(III) toward carboxylate bonding, conventional methods could not be used to obtain the desired Cr-soc-MOF. Accordingly, a novel method based on transmetalation of a template MOF into an exchanged MOF was developed as described herein. For example, the method may be based on post-synthetic metal cluster metathesis from a template MOF with a known structure to an isoreticular and/or isostructural chromium-based MOF.

Contacting generally refers to the act of touching, making contact, or of bringing to close or immediate proximity, including at the cellular or molecular level, for example, to bring about a physiological reaction, a chemical reaction, or a physical change (e.g., in solution, in a reaction mixture, in vitro, or in vivo). Contacting may refer to bringing two or more components in proximity, such as physically, chemically, electrically, or some combination thereof. Mixing, pouring, adding, etc. are examples of contacting. In many embodiments, the contacting is sufficient to bring about a reaction. For example, one or more of a pressure, temperature, and duration may be selected for the contacting. In an embodiment, the select temperature may be about 115° C. In an embodiment, the select period of time is greater than about 1 hour. In a preferred embodiment, the select period of time is about 20 to about 24 hours. In an embodiment, the contacting proceeds under an inert atmosphere. In an embodiment, the contacting proceeds under an inert atmosphere at about 115° C. for about 20 to 24 h.

The template MOF may be an Fe-based MOF with an underlying soc topology. In an embodiment, the Fe-soc-MOF may be fabricated prior to contacting. For example, Fe-soc-MOF may be fabricated via a solvothermal reaction between a tetratopic ligand (e.g., 3,3",5,5"-tetrakis(4-carboxyphenyl)-p-terphenyl ($H_4$TCPT)) and $FeCl_3.6H_2O$ in acidic solution containing a mixture of N,N'-dimethylformamide (DMF) and acetonitrile ($CH_3CN$) to form homogenous crystals of Fe-soc-MOF. Any of the ligands of the present disclosure may be used herein. In an embodiment, the Fe-soc-MOF may be characterized by the formula [$Fe_3$($\mu_3$-O)($H_2O$)$_2$(TCPT)$_{1.5}$Cl].

The template MOF may be contacted with a reactant including chromium in a presence of a solvent. In many embodiments, the reactant including chromium is $CrCl_2$. In many embodiments, the solvent is dimethylformamide (DMF).

In an embodiment, the method may further comprise one or more of soaking in a solvent (e.g., acetonitrile) for a period of time (e.g., about 6 h, about 12 h, about 24 h); exchanging with a solvent (e.g., acetone) for about the same period of time; and activating the Cr-soc-MOF (e.g., Cr-soc-MOF-1) at elevated temperature (e.g., about 120° C.).

The resulting exchanged MOF may be a chromium-based metal-organic framework with soc topology. For example, the exchanged MOF may be characterized by the formula Cr-soc-MOF. In many embodiments, Fe from the Fe-soc-MOF is replaced by, or exchanged with, Cr from the reactant including chromium. In an embodiment, the method includes a single-crystal to single-crystal transformation of a [$Fe_3(\mu_3$-O)($O_2C^-$)$_6$] molecular building block (MBB) in Fe-soc-MOF-1 into [$Cr_3(\mu_3$-O)($O_2C^-$)$_6$] MBB to form isostructural and/or isoreticular Cr-soc-MOF-1 with near complete exchange of Fe for Cr. For example, in an embodiment, the exchanged MOF (e.g., Cr-soc-MOF) may contain about 98% chromium. In other embodiments, the exchanged MOF may contain more than about 98% chromium or less than about 98% chromium.

In an embodiment, an oxidation state of chromium may be (+III). In an embodiment, a counterion is present. For example, in an embodiment, the counter-ion is a counteranion. In an embodiment, the counterion is $Cl^-$. In an embodiment, a charge of the cationic trinuclear cluster [$Cr_3(\mu_3$-O)($O_2C$—)$_6$] is balanced by one $Cl^-$ anion per cluster.

The Cr-soc-MOF may exhibit a single crystal structure. In an embodiment, the structure of Cr-soc-MOF may include well-defined 1D infinite channels and cubic-shaped cages constructed by six TCPT$^{4-}$ ligands, which occupy the faces of the cage, and eight inorganic trinuclear Cr(III) clusters located on the vertices of the cuboidal cage. The dimension of the channels in Cr-soc-MOF may be about 17 Å, falling approximately at the borderline of micro- and mesoporous materials.

Method of Sorbing Water Vapor Using Cr-soc-MOF

Figure 2:
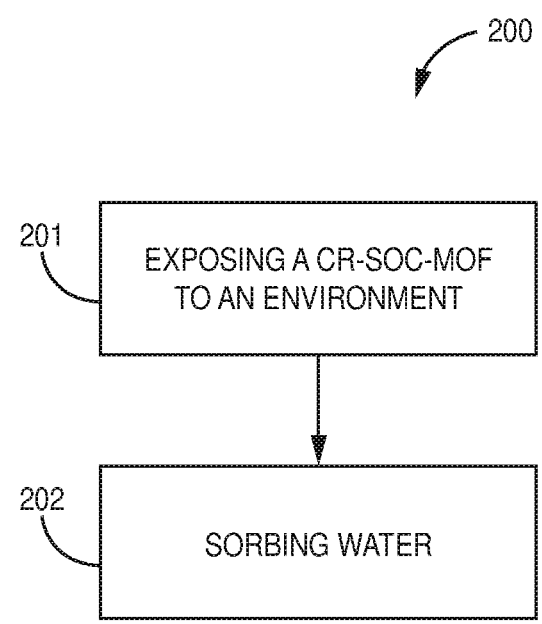
FIG. 2 is a flowchart of a method of adsorbing water vapor, according to one or more embodiments of the present disclosure.

FIG. 2 is a flowchart of a method 200 of sorbing water vapor, according to one or more embodiments of the present disclosure. The method 200 comprises exposing 201 a Cr-soc-MOF to an environment and sorbing 202 water vapor using the Cr-soc-MOF.

At step 201, a Cr-soc-MOF is exposed to an environment. Exposing generally refers to subjecting to any conditions of the environment. For example, exposing may include subjecting to one or more of a temperature, pressure, and chemical species present in the environment. In many embodiments, the environment includes a confined space or a nearly confined space. In other embodiments, the environment is an open space. The environment may be characterized by a relative humidity (RH) ranging from about 0% RH to about 100% RH. In an embodiment, the relative humidity may range from one or more of about 25% to about 65%, about 35% to about 65%, about 25% to about 75%, and about 25% to about 85%. In many embodiments, conditions of the environment include about ambient temperature and pressure. For example, in an embodiment, a condition of the environment is about room temperature and/or about atmospheric pressure. The Cr-soc-MOF may include any of the embodiments described herein.

At step 202, the Cr-soc-MOF is used for sorbing water vapor. Sorbing generally refers to one or more of adsorbing, absorbing, and desorbing. In many embodiments, sorbing or sorption refers to adsorbing and desorbing. In an embodiment, sorbing includes adsorbing. In an embodiment, sorbing includes desorbing. Sorbing may include one or more of selective sorption, sequential sorption, and simultaneous sorption. In an embodiment, sorbing includes selective sorption, such as sorption of a single compound. In an embodiment, sorbing includes subsequent sorption, such as sorption of a first compound and then a second compound. In an embodiment, sorbing includes simultaneous sorption, such as sorption of two or more compounds at about the same time. In many embodiments, sorption includes sorption of a single compound.

In an embodiment, the Cr-soc-MOF adsorbs water vapor as a relative humidity of the environment increases. The Cr-soc-MOF's adsorption of water vapor may be characterized by an S-shaped or S-shaped-like form of an adsorption isotherm. For example, in an embodiment, the Cr-soc-MOF's adsorption of water vapor may be characterized by one or more phases. In an embodiment, adsorption gradually increases up to about a first relative humidity. In an embodiment, a steep uptake of water is observed after a second relative humidity. In an embodiment, a maximum water uptake may be observed at a third relative humidity. In an embodiment, adsorption gradually increases up to about 55% relative humidity (e.g., a first relative humidity), a steep uptake of water may be observed at about 60% relative humidity to about 75% relative humidity, and a maximum water uptake may be observed at about 75% relative humidity. In an embodiment, the Cr-soc-MOF may adsorb up to about 200 wt. % of adsorbed water per gram of sorbent at the third relative humidity (e.g., at about 75% relative humidity). In an embodiment, a mass of adsorbed water vapor is about two times a weight of the Cr-soc-MOF.

In an embodiment, the Cr-soc-MOF desorbs water vapor as a relative humidity of the environment decreases. The Cr-soc-MOF desorption of water vapor may proceed at ambient temperatures and pressures. For example, in an exemplary embodiment, adsorbed water vapors may be completely desorbed at about room temperature by simply reducing a relative humidity of the environment. In another exemplary embodiment, adsorbed water vapors may be completely desorbed at about room temperature by simply reducing a relative humidity of the environment, without heating and/or without applying evacuation. In an embodiment, adsorbed water vapors may be completely desorbed by reducing relative humidity to about 25%. In this way, the Cr-soc-MOF provides a highly efficient and cost effective recycling process.

In an embodiment, the exceptional properties of the Cr-soc-MOF may be preserved after extensive absorption-desorption cycles. In particular, the Cr-soc-MOF may be stable over about 100 adsorption-desorption cycles or relative humidity swings. In an embodiment, the water uptake and shape of adsorption isotherms may be preserved after multiple relative humidity swings and/or adsorption-desorption cycles. In an embodiment, the water uptake and shape of adsorption isotherms may be preserved even after more than 100 adsorption-desorption cycles or relative humidity swings. For example, in an embodiment, the relative humidity swings may range from about 25% to about 85% relative humidity.

Gas Storage

Figure 3:
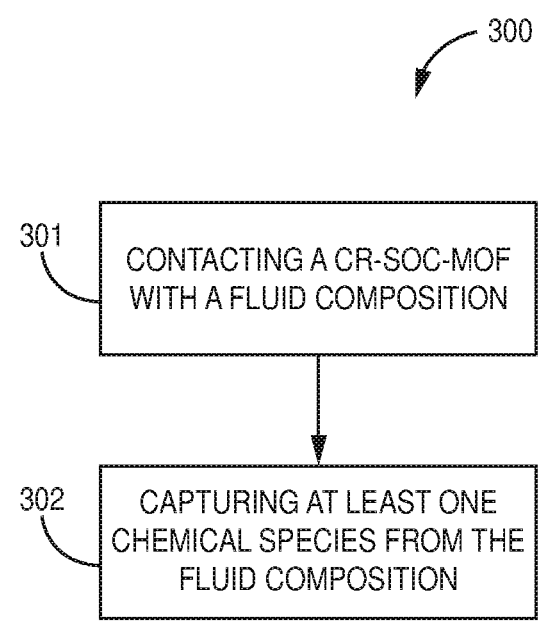
FIG. 3 is a flowchart of a method of capturing one or more chemical species, according to one or more embodiments of the present disclosure.

FIG. 3 is a flowchart of a method 300 of sorbing one or more chemical species. The method 300 comprises contacting 301 a Cr-soc-MOF with a fluid composition and capturing 302 at least one chemical species from the fluid composition. The method may be used for storing one or more chemical species, including gaseous chemical species. In this way, the Cr-soc-MOFs exhibit exceptionally high gas storage uptake.

At step 301, a Cr-soc-MOF is contacted with a fluid composition. Contacting may refer to, among other things, feeding or flowing a fluid composition sufficient to bring the Cr-soc-MOF in contact with at least one chemical species of the fluid composition. In many embodiments, the contacting proceeds at high pressure. For example, the pressure may range from about 25 bar to about 100 bar. In many embodiments, the pressure ranges from about 35 bar to about 80 bar. For example, in an embodiment, the pressure is about 35 bar. In an embodiment, the pressure is about 65 bar. In an embodiment, the pressure is about 80 bar. In many embodiments, the contacting may proceed across a wide range of temperatures. For example, the temperature may range from about 200 K to about 500 K. In many embodiments, the temperature ranges from about 250 K to about 300 K. For example, in an embodiment, the temperature is about 250 K, about 260 K, about 270 K, about 280 K, about 298K, or about 300 K.

Any of the Cr-soc-MOFs described herein may be used herein. The fluid composition may include one or more chemical species. The one or more chemical species may include one or more of $CH_4$, $O_2$, $CO_2$, $H_2$, and $H_2O$. The one or more chemical species may be present as one or more of a solid, liquid, vapor, or gas. In many embodiments, the chemical species are present as a gas and/or vapor.

At step 302, at least one chemical species from the fluid composition is captured. Capturing may include sorbing one or more chemical species from the fluid composition. In many embodiments, one or more of $CH_4$, $O_2$, $CO_2$, $H_2$, and $H_2O$ are captured. In an embodiment, $CH_4$ is the captured chemical species. In an embodiment, $O_2$ is the captured chemical species. In an embodiment $CO_2$ is the captured chemical species. In an embodiment, $H_2$ is the captured chemical species. In an embodiment, $H_2O$ is the captured chemical species.

Applications

The Cr-soc-MOF may be used in any of wide range of applications. Any of the Cr-soc-MOFs and embodiments thereof of the present disclosure may be used herein.

Embodiments of the present disclosure describe adsorption heat pumps comprising Cr-soc-MOF. Embodiments of the present disclosure describe desiccant cooling systems comprising Cr-soc-MOF. Such systems are superior to conventional systems. For example, the adsorbed water can be desorbed from the solid adsorbent under mild conditions. Water molecules may be completely or nearly completely desorbed at about 25% RH. In addition, an exceptionally large amount of adsorbed water (about 1.95 g/g) can be desorbed from the Cr-soc-MOF without heating or applying evacuation. In this way, the use of Cr-soc-MOF allows the operation of AHP and DCS systems with extremely high efficiency to produce heat and cooling power using just relative humidity gradient or pressure gradient.

Embodiments of the present disclosure describe a dehumidification and humidity control in enclosed areas (e.g., nearly enclosed areas) and confined spaces (e.g., nearly confined spaces). The Cr-soc-MOF may effectively adsorb water vapor when the moisture level is sufficient high and desorb when the surround atmosphere is characterized as dry. Any of the relative humidity ranges described in the present disclosure may be used herein.

Embodiments of the present disclosure describe adsorption desalination comprising the Cr-soc-MOF. In many embodiments, the adsorption and desorption to regenerate potable water is achieved via one or more of pressure swing adsorption and relative humidity swing adsorption.

The following Examples are intended to illustrate the above invention and should not be construed as to narrow its scope. One skilled in the art will readily recognize that the Examiners suggest many other ways in which the invention could be practiced. It should be understand that numerous variations and modifications may be made while remaining within the scope of the invention.

Example 1

Materials and Methods

Iron(III) chloride hexahydrate (FeCl$_3$.6H$_2$O), chromium (II) chloride anhydrous (CrCl$_2$), N,N-dimethylformamide (DMF), acetonitrile and nitric acid were purchased from commercial sources and were used without further purification. Details on the synthesis of the organic ligand used in this study, 3,3",5,5"-tetrakis(4-carboxyphenyl)-p-terphenyl (H$_4$TCPT) is reported in the literature. Although H$_4$TCPT is used herein, any ligand characterized by the chemical formula below may be used:

diffractometer at 45 kV and 40 mA for Cu K$\alpha\lambda$=1.5418 Å) equipped with a variable-temperature stage. The sample was held at the designated temperature for at least 10 min between each scan. Single-crystal X-ray diffraction data were collected using a Bruker X8 PROSPECTOR APEX2 CCD diffractometer (Cu K$\alpha$, $\lambda$=1.54178 Å). Indexing was performed using APEX2 (Difference Vectors method). Data integration and reduction were performed using SaintPlus 6.01. Absorption correction was performed by multi-scan method implemented in SADABS. Space groups were determined using XPREP implemented in APEX2. Structure was solved using SHELXS-97 (direct methods) and refined using SHELXL-97 (full-matrix least-squares on F$^2$) contained in APEX2. Crystal data and refinement conditions are shown in Table 1 and 2. Low-pressure gas sorption measurements were performed on a fully automated Autosorb-IQ gas sorption analyzer (Quantachrome Instruments). Low-pressure gas adsorption studies were conducted on a fully automated micropore gas analyzer Autosorb-IQ (Quantachrome Instruments) at relative pressures up to 1 atm. The temperature was controlled using a cryocoller system (cryogen-free) capable of temperature control from 20 to 320 K.

Figure 4:
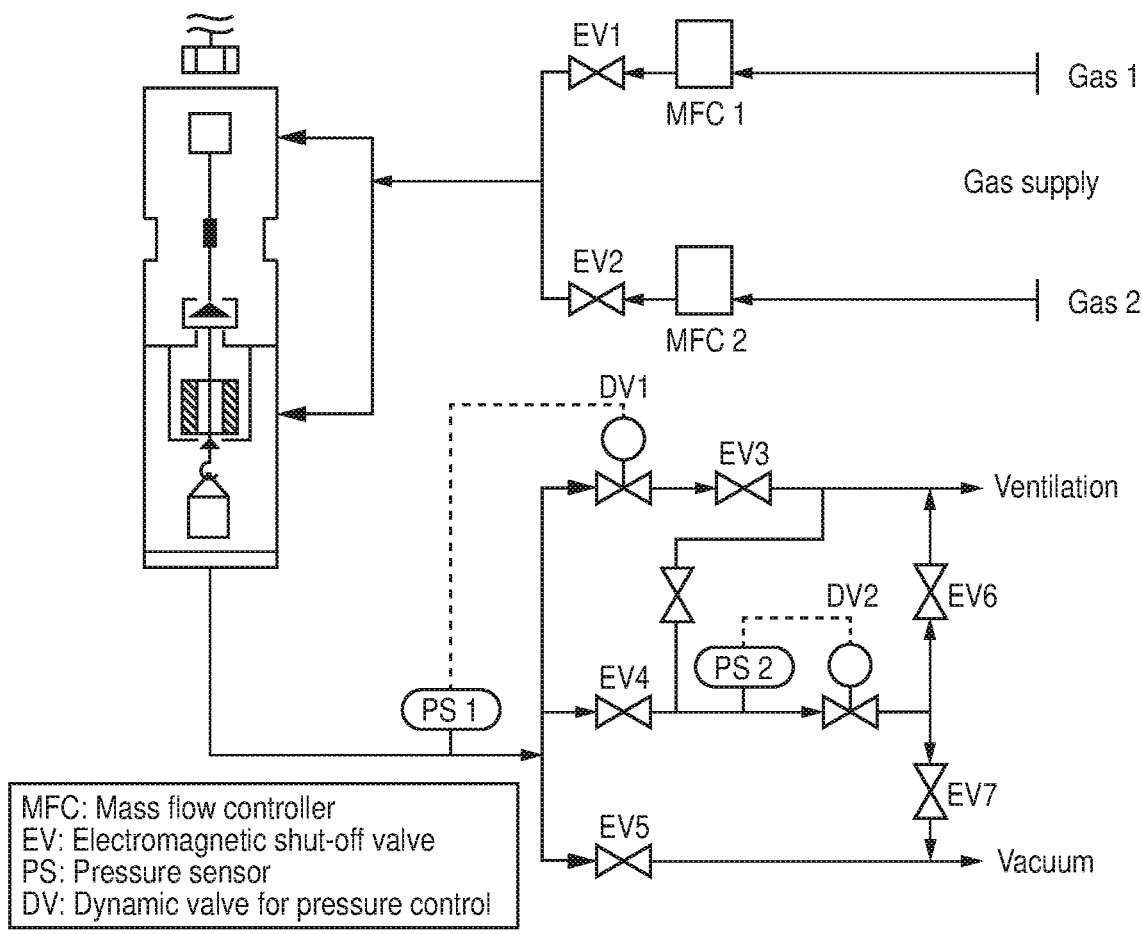
FIG. 4 is a representation of the Rubotherm gravimetric-densimetric apparatus, according to one or more embodiments of the present disclosure.

High-pressure gas adsorption studies were performed on a magnetic suspension balance marketed by Rubotherm (Germany) Type Adsorption equilibrium measurements of pure gases were performed using a Rubotherm gravimetric-densimetric apparatus G-Hp-Flow (FIG. 4), composed mainly of a magnetic suspension balance (MSB) and a network of valves, mass flow meters, and temperature and pressure sensors. The MSB overcame the disadvantages of other commercially available gravimetric instruments by separating the sensitive microbalance from the sample and the measuring atmosphere, and was able to perform adsorption measurements across a wide pressure range (i.e., from 0 to 20 MPa). The adsorption temperature was controlled within the range of 77 K to 423 K. In a typical adsorption experiment, the adsorbent was precisely weighed and placed

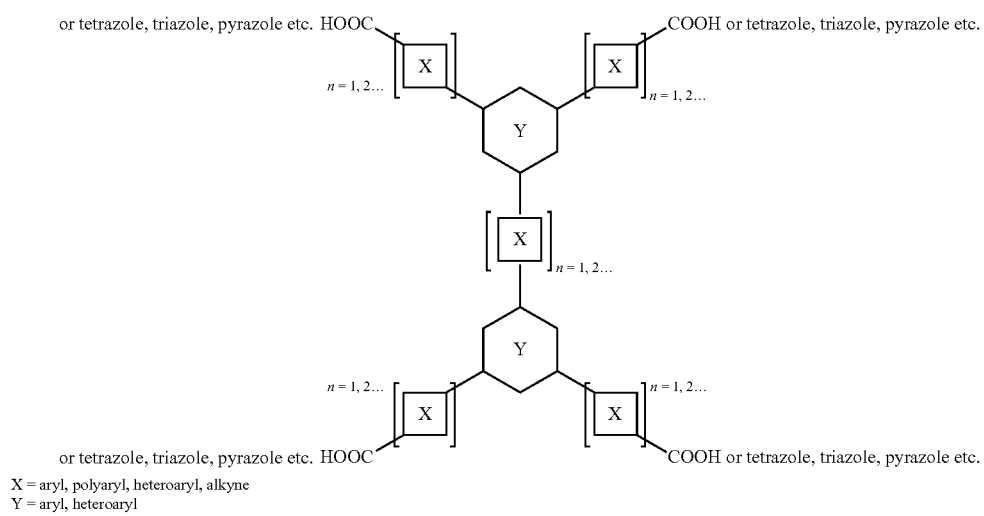

X = aryl, polyaryl, heteroaryl, alkyne
Y = aryl, heteroaryl

Fourier-transform infrared (FT-IR) spectra (4000-650 cm$^{-1}$) were collected in the solid state on a Nicolet 700 FT-IR spectrometer. The peak intensities were described in each of the spectra as broad (br), strong (s), medium (m), weak (w). Powder X-ray diffraction (PXRD) measurements were performed on a PANalytical MPD X'Pert PRO X-ray in a basket suspended by a permanent magnet through an electromagnet. Then the cell housing the basket was closed and vacuum or high pressure was applied. The gravimetric method allowed the direct measurement of the reduced gas adsorbed amount (□). Correction for the buoyancy effect was required to determine the excess and absolute adsorbed amount using equations 1 and 2, where $V_{adsorbent}$ and $V_{ss}$ and $V_{adorbed}$ phase refer to the volume of the adsorbent, the volume of the suspension system, and the volume of the adsorbed phase, respectively.

$$\Omega = m_{absolute} - \rho_{gas}(V_{adsorbent} + V_{ss} + V_{adsorbed\text{-}phase}) \qquad (1)$$

$$\Omega = m_{excess} - \rho_{gas}(V_{adsorbent} + V_{ss}) \qquad (2)$$

The buoyancy effect resulting from the adsorbed phase was taken into account via correlation with the pore volume or with the theoretical density of the sample.

These volumes were determined using the helium isotherm method by assuming that helium penetrated in all open pores of the material without being adsorbed. The density of the gas was determined using the Refprop equation of state (EOS) database and checked experimentally using a volume-calibrated titanium cylinder. By weighing this calibrated volume in the gas atmosphere, the local density of the gas was determined. Therefore, simultaneous measurement of adsorption capacity and gas-phase density as a function of pressure and temperature was possible.

The pressure was measured using two Drucks high-pressure transducers ranging from 0.5 to 34 bar and 1 to 200 bar, respectively, and one low pressure transducer ranging from 0 to 1 bar. Prior to each adsorption experiment, about 100 mg of the sample was outgassed at 393 K for 12 hours under a residual pressure of $10^{-6}$ mbar. The temperature during adsorption measurements was maintained constant using a thermostat-controlled circulating fluid.

Scanning Electron Microscopy (SEM) images and Energy Dispersive X-ray Spectroscopy (EDX) were performed on FEI Quanta 600 electron microscope equipped with X-ray mapping with acceleration voltage of 30 kV.

Inductively coupled plasma-Optical emission spectroscopy was carried out using a Varian 720 ICP-OES Spectrometer.

X-ray photoelectron spectroscopy (XPS) studies were carried out in a Kratos Axis Ultra DLD spectrometer equipped with a monochromatic Al K$\alpha$ x-ray source (hv=1486.6 eV) operating at 150 W, a multichannel plate and delay line detector under a vacuum of $1\sim10^{-9}$ mbar. The high-resolution spectra were collected at fixed analyzer pass energies of 20 eV. Sample was mounted in floating mode in order to avoid differential charging. Charge neutralization was required for all samples. Binding energies were referenced to the sp$^3$ hybridized (C—C) carbon for the C is peak set at 284.8 eV. XPS investigations were performed to characterize the chemical composition of the surface of the powdered samples and to determine the oxidation state of chromium in the Cr-soc-MOF-1. High-resolution XPS spectra of Cr 2p and Cl 2p core levels were obtained from Cr-soc-MOF-1 complex powder.

The$^+$ Cr 2p region showed one doublet situated at 576.6 eV and 586.3 eV corresponding to Cr 2p$_{3/2}$ and Cr 2p$_{1/2}$ spin-orbit split components, respectively. Additionally, a satellite structure was observed at 598.4 eV corresponding to a shake-up satellite for Cr 2p$_{1/2}$ component. The satellite peak of Cr 2p$_{3/2}$ component strongly overlaps with Cr 2p$_{1/2}$ peak. The binding energies of the components of Cr 2p doublet and their corresponding satellites were characteristic of Cr$^{3+}$ oxidation state of chromium. The Cl 2p region showed one doublet situated at 198.5 eV and 200.1 eV corresponding to Cl 2p$_{3/2}$ and Cl 2p$_{1/2}$ spin-orbit split components respectively. The Cr:Cl ratio was obtained using XPS by applying the appropriate relative sensitivity factors (RSFs) for the Kratos Axis Ultra DLD instrument to the integrated peak areas of the Cr 2p and Cl 2p core levels. The Cr:Cl ratio was found to be equal to 3:1.

Water sorption experiments were carried out using a VTI-SA vapor sorption analyzer from TA Instruments (New Castle, Del., United States). The water vapor activity was controlled automatically by mixing wet vapor feed with a dry N$_2$ line; hence, N$_2$ acts as a carrier gas for water vapor. The sample "dry mass" was measured under N$_2$ and was at equilibrium before introducing water vapor into the chamber. The adsorption isotherms, obtained at equilibrium, were collected within a range of 0%-90% RH. The acetone exchanged sample was activated at 120° C. prior to sorption experiment for 8 hrs. The maximum equilibrium time for each RH was maintained 2 hrs. The cycles were carried out in the RH value between 25% and 85% with maximum equilibrium time 3 hrs.

Experimental Procedures

Synthesis of Fe-soc-MOF-1 (1)

Figure 5:
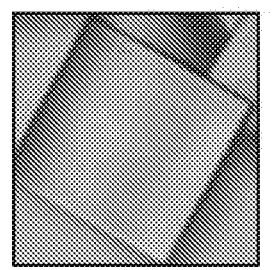
FIG. 5 are optical microscope images of Fe-soc-MOF-1 and Cr-soc-MOF-1 single crystals, according to one or more embodiments of the present disclosure.
Figure 5:
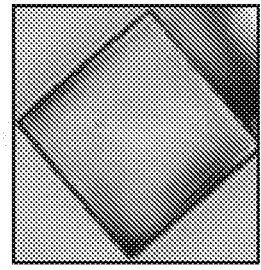

A solution of FeCl$_3$. 6H$_2$O in DMF (0.1 M, 0.3 mL, 0.03 mmol) was added to a mixture of H$_4$TCPT (7.1 mg, 0.01 mmol), DMF (1 mL) and acetonitrile (1 mL) in a 20 mL scintillation vial. Dilute nitric acid solution in DMF (3.5 M, 1.5 mL) was added to the reaction mixture followed by sonication. The clear orange-yellow solution was subsequently placed into a preheated oven at 115° C. for 3 d to give pure small orange-yellow cube-shaped crystals (FIG. 5). Crystals were washed 4-5 times with DMF. FT-IR (4000-650 cm-1): 3360 (br), 2971 (w), 1652 (s), 1593 (s), 1400 (s), 1254 (w), 1185 (w), 1092(m), 1046 (s), 1016 (w), 859 (w), 836 (w), 782 (s), 701 (w).

Synthesis of Cr-soc-MOF-1 (2)

The Fe-soc-MOF-1 crystals were washed with acetonitrile quickly 3-4 times to remove the surface DMF. Finally, washing was accomplished with acetone 1-2 times and the compound was transferred to an inert atmosphere glove box. Inside the glove box, about 25 mg of the Fe-soc-MOF-1 was weighed in a 20 mL scintillation vial. In another vial, 150 mg of CrCl$_2$ was dissolved in 3 mL DMF, resulting in a light skyblue clear solution. The solution was then added carefully to the former vial. An immediate color change to green was observed. The vial was capped, taken out from glovebox and incubated at 115° C. for 20 h. The vial was then allowed to cool to room temperature. The dark green supernatant solution was removed and the resulting green crystals of Cr-soc-MOF-1 (FIG. 5) were washed 4-5 times with DMF. FT-IR (4000-650 cm-1): 3334 (br), 2971 (w), 1654 (s), 1598 (s), 1553 (w), 1400 (s), 1253 (w), 1186 (w), 1088 (m), 1045 (s), 1016 (w), 879 (w), 861 (w), 780 (s), 701 (m).

Results and Discussion

Synthesis and Characterizations of Cr-Soc-MOF-1

Figure 6:
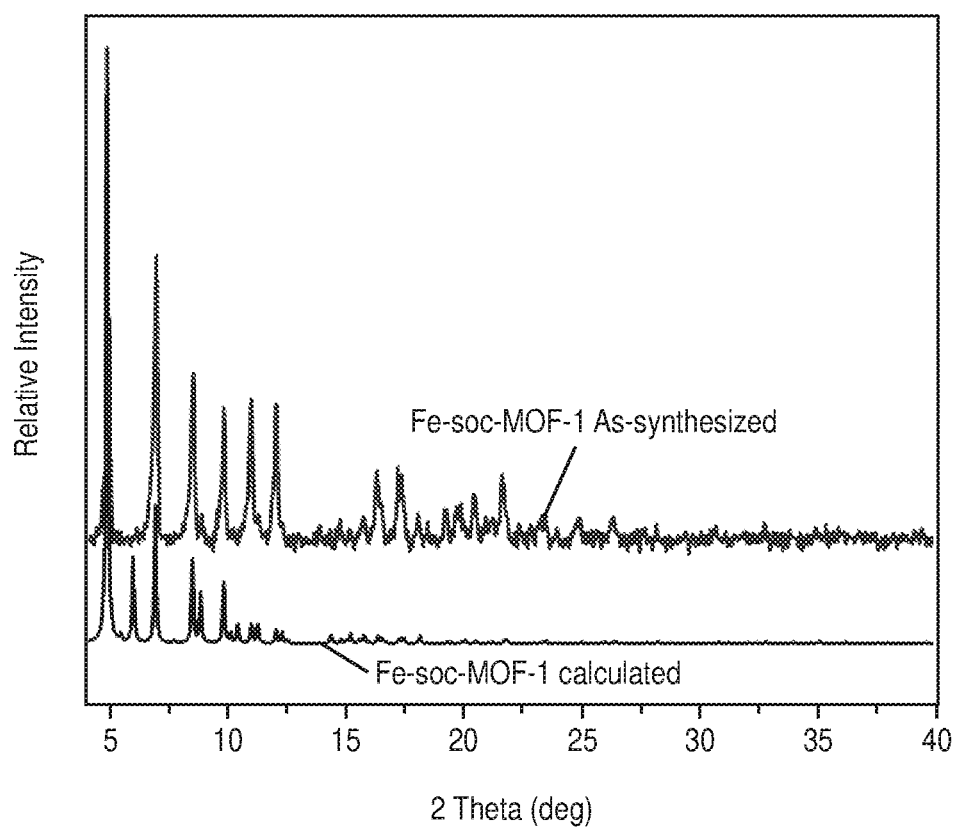
FIG. 6 is a graphical view of calculated and experimental PXRD patters for the Fe-soc-MOF-1, according to one or more embodiments of the present disclosure.
Figure 7A:
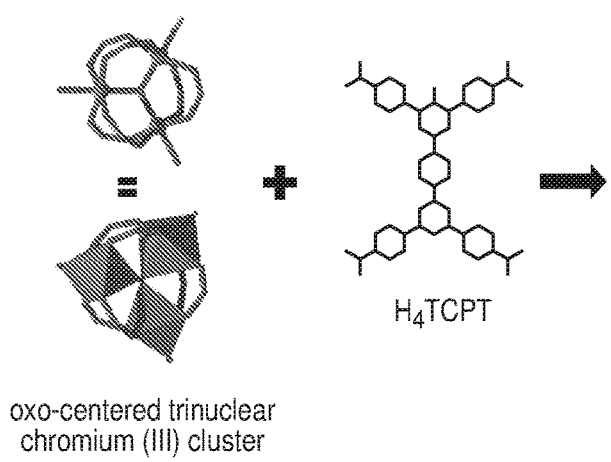
FIGS. 7A-7B is a schematic diagram of select fragments from the crystal structure of Cr-soc-MOF-1, where (7A) is a schematic diagram of $\mu_3$-oxygen-centered trinuclear Cr (III) carboxylate clusters and the deprotonated organic linker (e.g., $H_4TCPT$) and (7B) is a schematic diagram illustrating the well-defined channels and cages found in Cr-soc-MOF-1 (color code: C=gray; O=red; Cl=pink, and Cr=green; hydrogen atoms are omitted for clarity), according to one or more embodiments of the present disclosure.
Figure 7B:
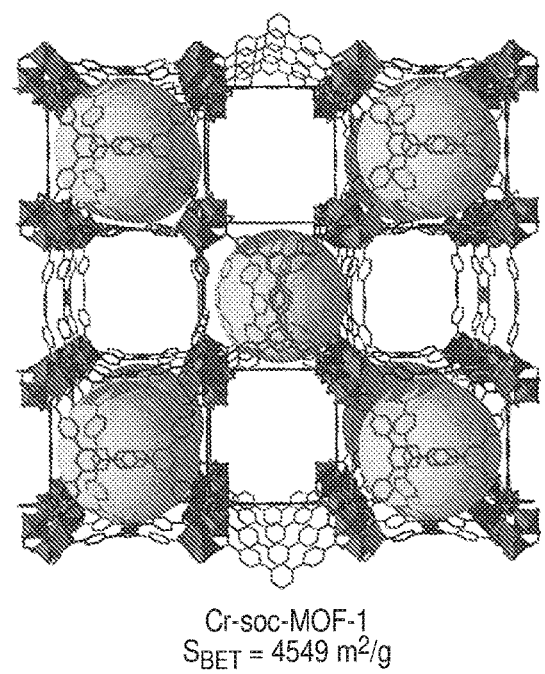
Figure 8:
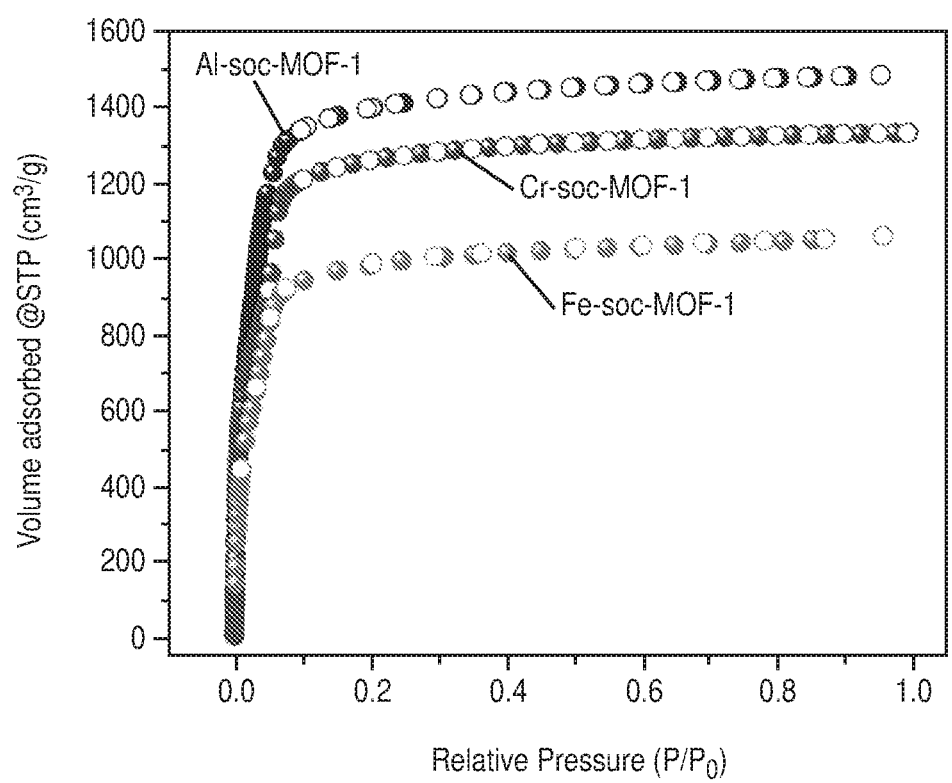
FIG. 8 is a comparison of nitrogen adsorption isotherm at 77 K for Al-soc-MOF-1, Cr-soc-MOF-1, and Fe-soc-MOF-1, according to one or more embodiments of the present disclosure.

During initial efforts to isolate the isostructural chromium-soc-MOF analogue, countless attempts to isolate the reaction conditions that consistently allowed the in situ formation of the desired trinuclear chromium (III) MBB were unsuccessful. Accordingly, research efforts were directed to another alternative route based on the transmetalation of the synthesized Fe-soc-MOF into the looked-for Cr-soc-MOF. Accordingly, a solvothermal reaction between the tetratopic ligand 3,3",5,5"-tetrakis(4-carboxyphenyl)-p-terphenyl (H$_4$TCPT) and FeCl$_3$.6H$_2$O in acidic solution containing a mixture of N,N'-dimethylformamide (DMF) and acetonitrile ($CH_3CN$) afforded yellow-orange cube-shape homogeneous crystals of Fe-soc-MOF-1 (1). Single-crystal X-ray diffraction (SCXRD) analysis and Powder X-ray diffraction (PXRD) pattern (FIG. 6) confirmed that 1 was isostructural to the reported Al-soc-MOF-1 with the formula $[Fe_3(\mu_3\text{-}O)(H_2O)_2(TCPT)_{1.5}Cl]$ (Table 1). Subsequently, the reaction of the yellow-orange colored crystals of Fe-soc-MOF-1 with $CrCl_2$ in DMF under inert atmosphere at 115° C. for a period of 24 h afforded the formation of dark green Cr-soc-MOF-1 single crystals (2) with nearly complete exchange of iron by chromium as supported by ICP-OES analysis, which revealed that Cr-soc-MOF-1 contained ~98% chromium. Furthermore, the single crystal structure of Cr-soc-MOF-1 was analyzed by SCXRD studies. As envisioned, Cr-soc-MOF-1 structure enclosed well-defined 1D infinite channels and cubic-shaped cages constructed by six $TCPT^{4-}$ ligands, which occupied the faces of the cage, and eight inorganic trinuclear Cr(III) clusters located on the vertices of the cuboidal cage (FIGS. 7A-7B). The structure of the Cr-soc-MOF-1 analogue slightly differed from the Al-soc-MOF-1 with regard to the size of the 1D channels and the cages: the channels in Cr-soc-MOF-1 were wider with an estimated dimension of ~17 Å taking van der Waals (vdW) radii into consideration, which was approximately at the borderline of micro-/mesoporous materials. This is also reflected from the shape of nitrogen adsorption isotherm as compared to the typical type I for the Al analogues (FIG. 8). The size of the cage in case of Cr-soc-MOF-1 was slightly smaller than the corresponding size of the Al analogue.

Figure 9A:
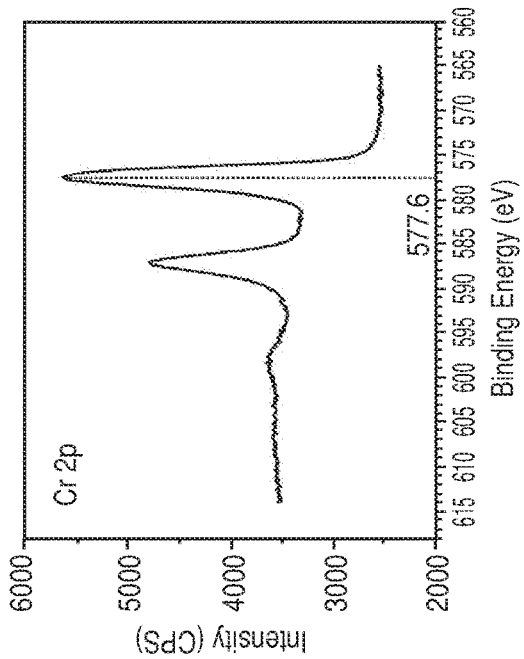
FIGS. 9A-9D illustrate structural characterizations of Cr-soc-MOF-1, where (9A) is an Energy-Dispersive X-ray Spectroscopy (EDS) elemental mapping analysis of Cr-soc-MOF-1, (9B) is a graphical view of high resolution X-ray photoelectron spectroscopy (XPS) spectrum of Cr 2p core level of the Cr-soc-MOF-1 sample, the binding energies of the components of Cr 2p doublet and their corresponding satellites are characteristic of Cr≠ oxidation state of chromium, (9C) is a graphical view of experimental and calculated PXRD patterns for Cr-soc-MOF-1, indicating the phase purity of the sample, and (9D) is a graphical view of nitrogen adsorption isotherm at 77 K on Cr-soc-MOF-1, according to one or more embodiments of the present disclosure.
Figure 9B:
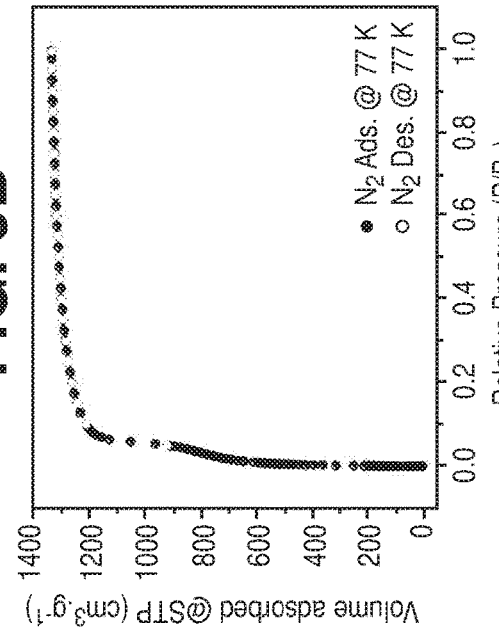
Figure 10:
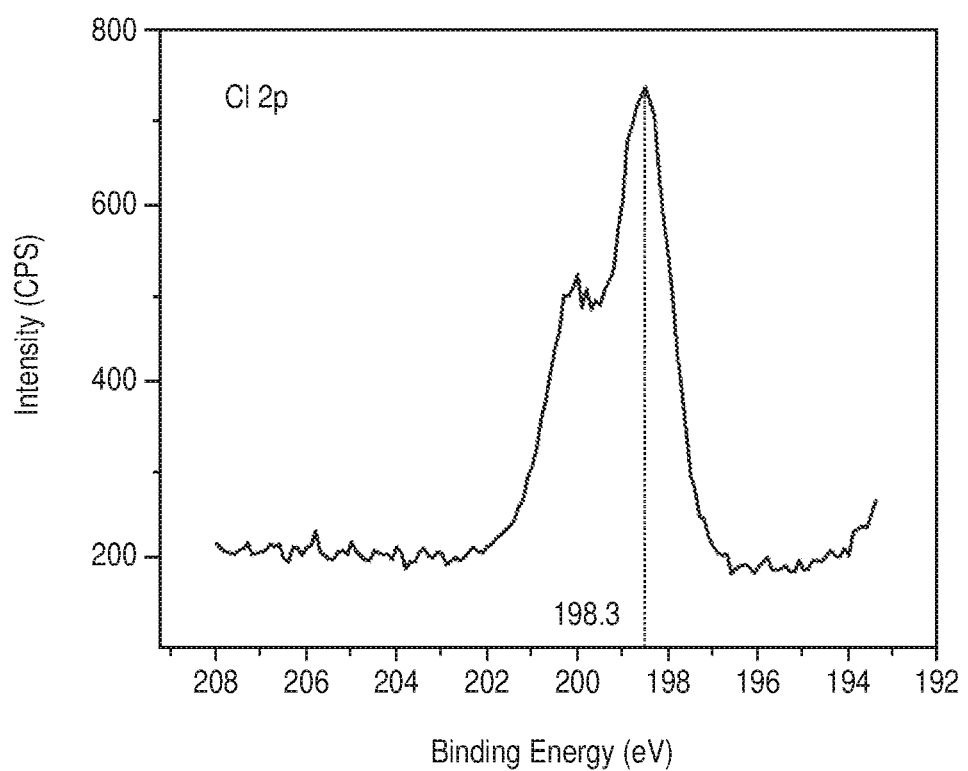
FIG. 10 is a high resolution XPS spectrum of Cl 2p core level of the Cr-soc-MOF-1 sample, according to one or more embodiments of the present disclosure.

The oxidation state of all chromium ions in Cr-soc-MOF-1 was (+III), as verified by X-ray photoelectron spectroscopy (XPS) studies (FIG. 9B). The charge of the cationic trinuclear cluster, $[Cr_3(\mu_3\text{-}O)(O_2C\text{—})_6]$, was balanced by one $Cl^-$ anion per cluster as supported by XPS data (FIG. 10). The efficiency of the performed metathesis was also confirmed by Energy-Dispersive X-ray Spectroscopy (EDS) elemental mapping analysis, which indicated that Cl, Cr and O were uniformly distributed on the crystal surface (FIG. 9A).

Figure 9C:
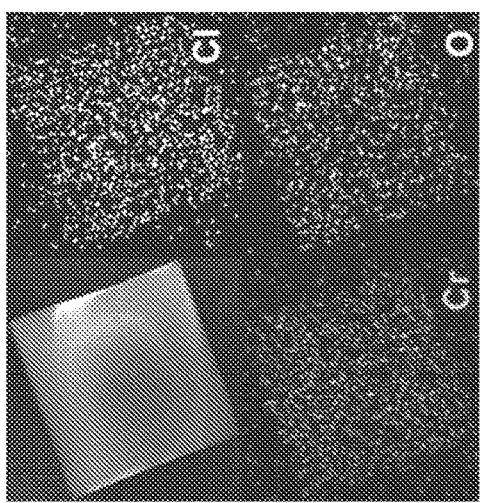
Figure 11:
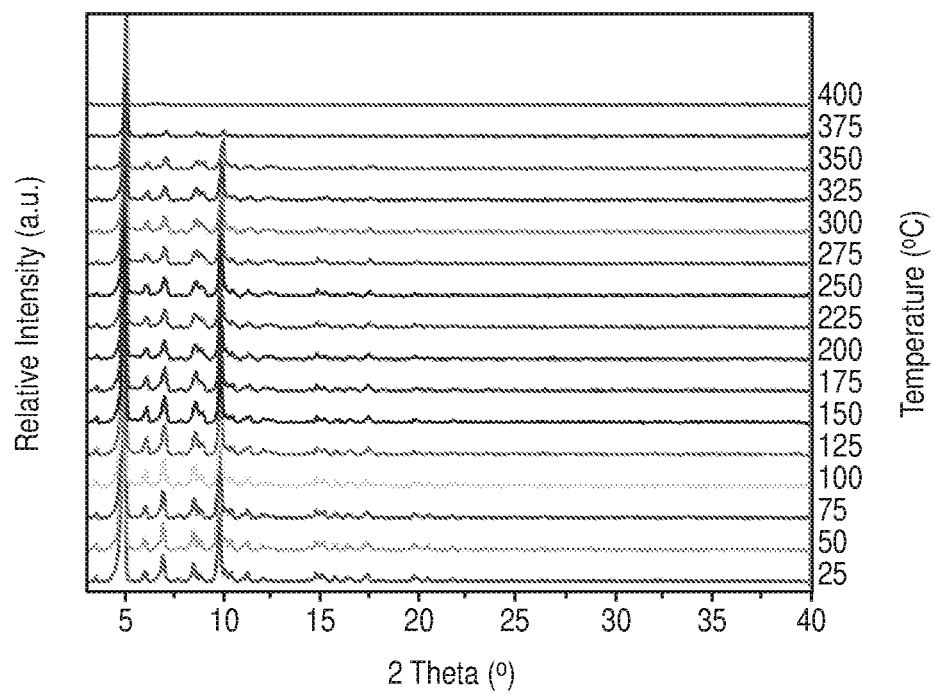
FIG. 11 is a VT-PXRD of acetane exchanged Cr-soc-MOF-1 from 25° C. to 400° C., according to one or more embodiments of the present disclosure.
Figure 12:
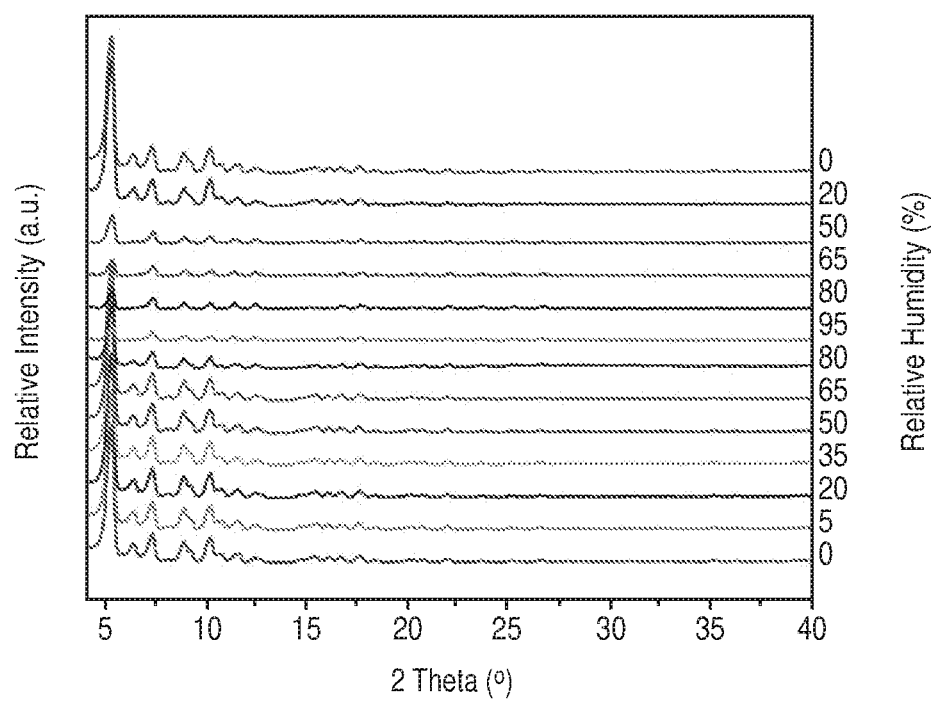
FIG. 12 is a powder x-ray diffraction (PXRD) of the acetone exchanged Cr-soc-MOF-1 under variable relative humidity, according to one or more embodiments of the present disclosure.
Figure 13:
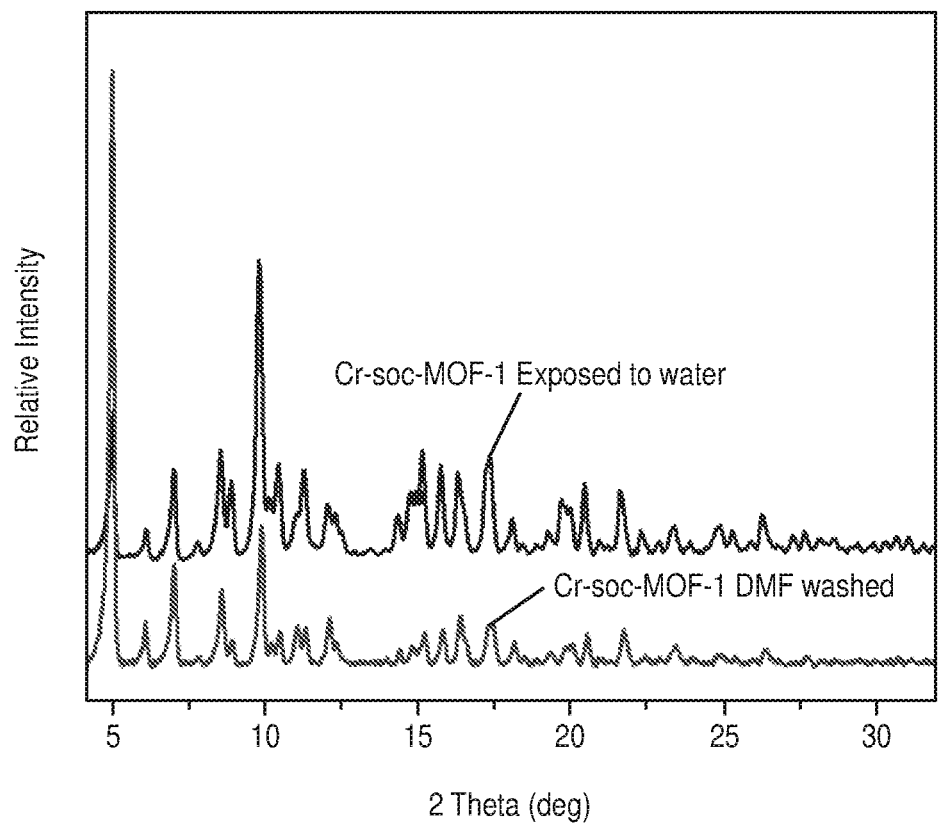
FIG. 13 is a graphical view of a comparison of experimental PXRD pattern of the Cr-soc-MOF-1 with the experimental PXRD pattern of the Cr-soc-MOF-1 exposed to water, according to one or more embodiments of the present disclosure.

The purity of compound 2 was confirmed by similarities between the experimental and calculated PXRD patterns (FIG. 9C). The Cr-soc-MOF-1 crystals, washed with DMF, were subjected to exchange with acetonitrile and acetone, respectively for 24 h and then used for further experiments. The high thermal stability of Cr-soc-MOF-1 was confirmed using variable-temperature PXRD studies (FIG. 11). Delightfully, variable humidity PXRD analysis (FIG. 12) showed that Cr-soc-MOF-1 was an exceptionally stable material towards prolonged exposure to moisture. It was to be noted that to the best of present knowledge, this was one of the rare highly porous MOFs with high stability in the presence of moisture. As a first test of water stability, Cr-soc-MOF-1 was soaked in liquid water at room temperature for 1 day without any structure/performance alteration. This unprecedented result was evidenced by the unchanged PXRD patterns of the pristine sample and the after soaking crystals in liquid water (FIG. 13).

Figure 9D:
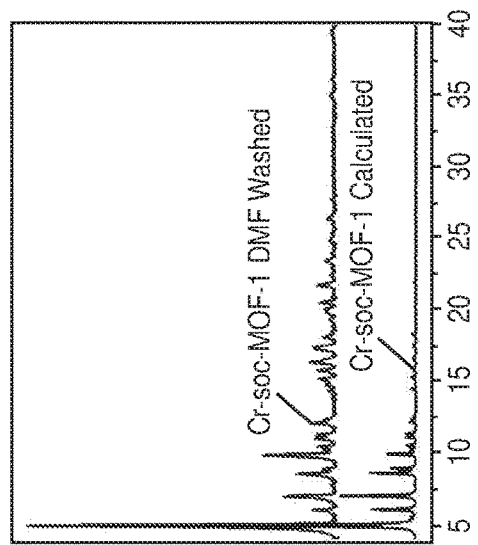
Figure 14:
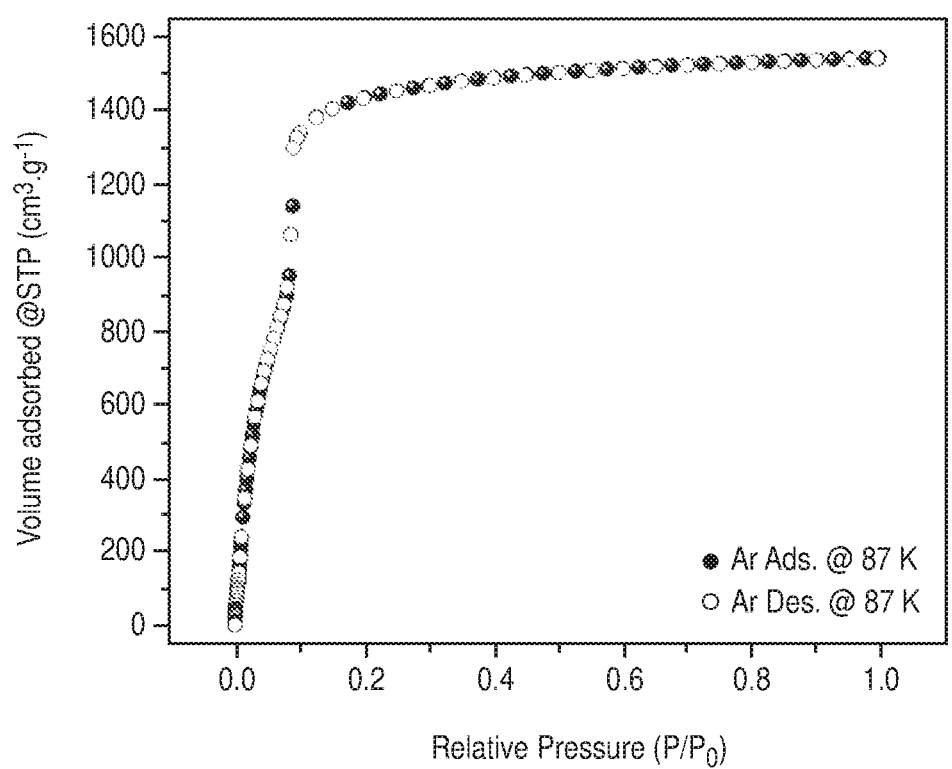
FIG. 14 is an argon adsorption isotherm at 87 K of freshly activated Cr-soc-MOF-1, according to one or more embodiments of the present disclosure.
Figure 15:
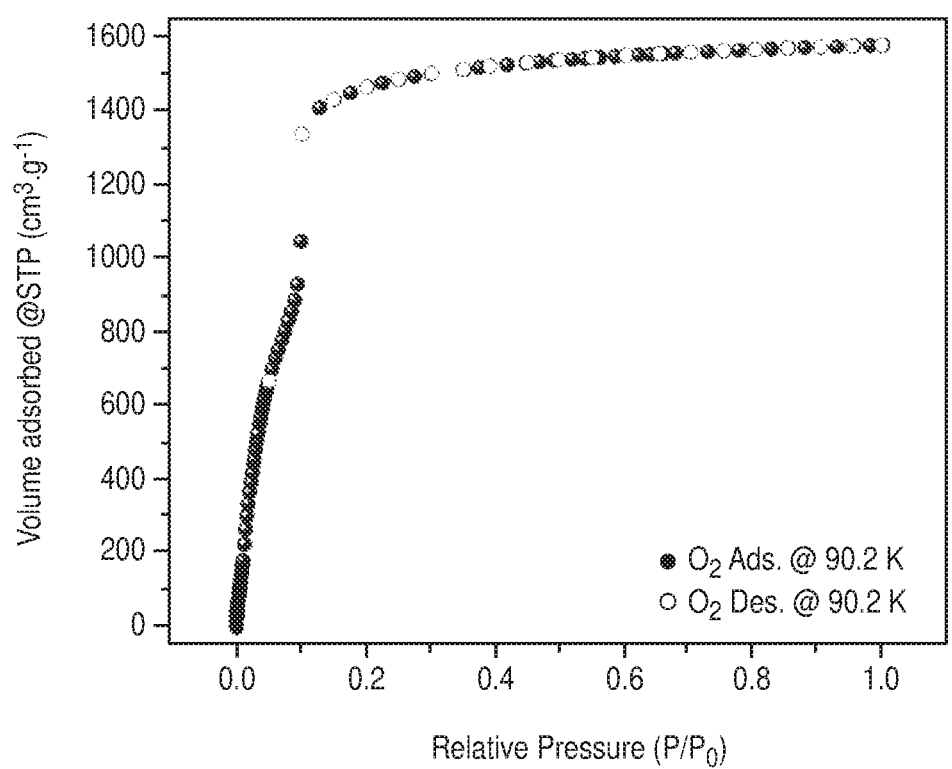
FIG. 15 is an oxygen adsorption isotherm at 90 K of freshly activated Cr-soc-MOF-1, according to one or more embodiments of the present disclosure.
Figure 16:
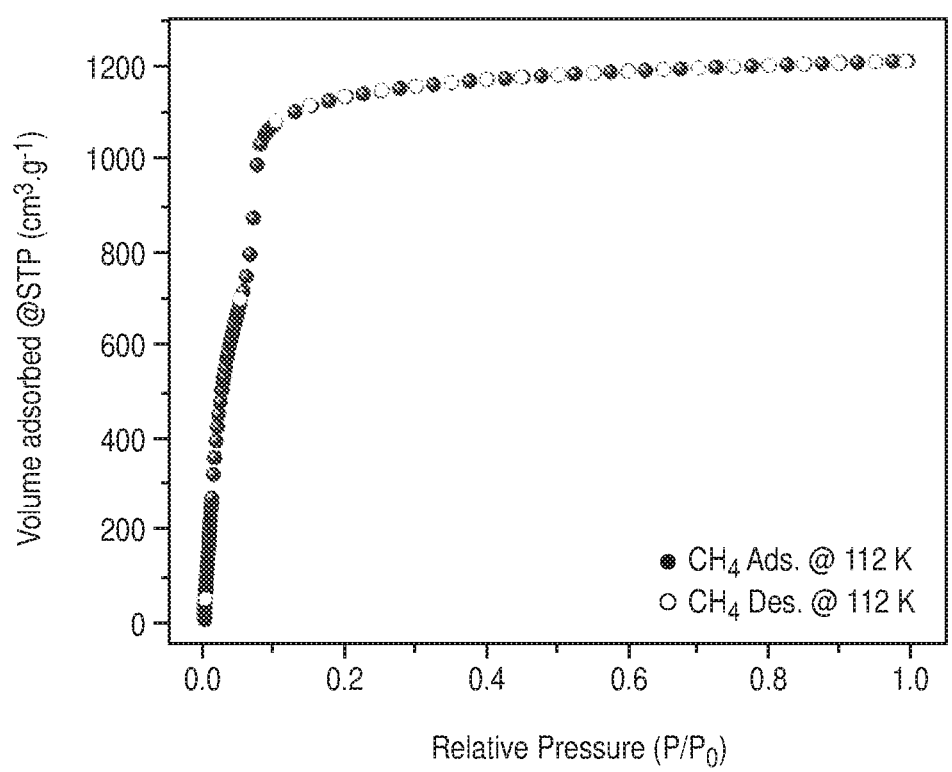
FIG. 16 is a methane sorption isotherm at 112 K of freshly activated Cr-soc-MOF-1, according to one or more embodiments of the present disclosure.
Figure 17:
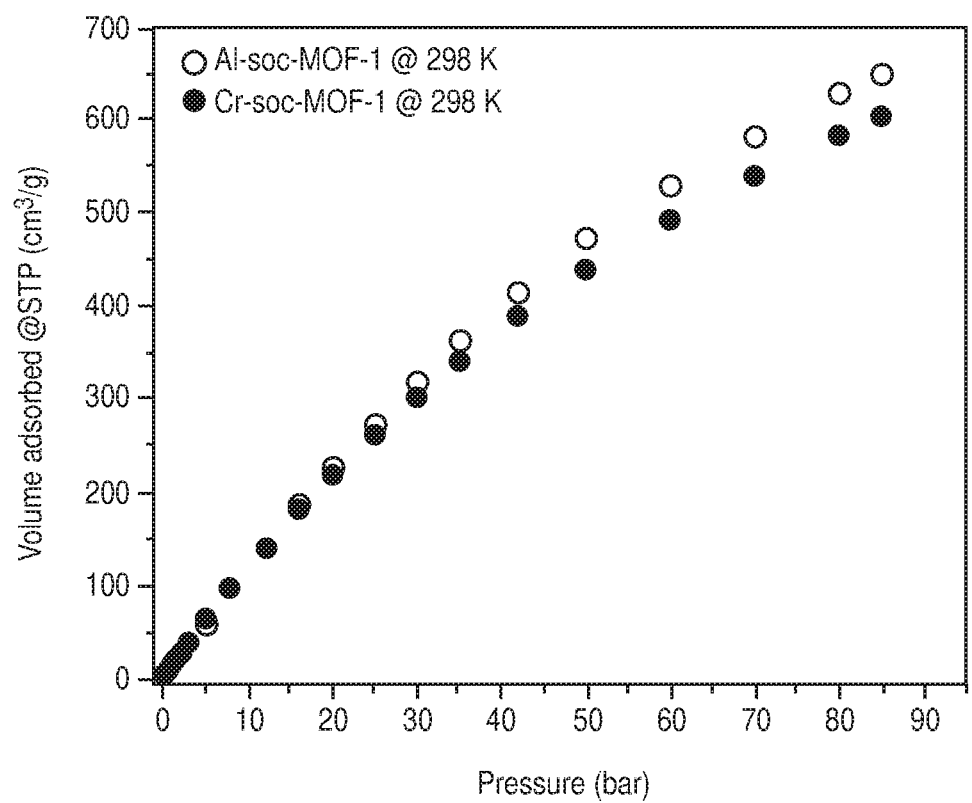
FIG. 17 is a comparison of methane sorption isotherm for Cr-soc-MOF-1 and Al-soc-MOF-1 up to 85 bar at 298 K, wherein it can be seen that both compounds have similar methane sorption properties and, as compared to Al-soc-MOF-1, Cr-soc-MOF-1 has slightly higher uptake at lower pressure due to stronger interaction and slightly lower uptake at higher pressure due to higher density, according to one or more embodiments of the present disclosure.

As in the case of the Al-soc-MOF-1, the guest solvents in the pore system of Cr-soc-MOF-1 were easily and fully removed using a traditional activation approach (vacuum and heating). The optimal porosity of Cr-soc-MOF-1 was obtained by heating at 120° C. under vacuum as supported by nitrogen and argon sorption isotherms (FIG. 9D and FIG. 14). The calculated apparent BET surface area and pore volume were 4549 $m^2/g$ and 2.1 $cm^3/g$, respectively, which was in good agreement with the theoretical values ($PV_{theo}$ 2.2 $cm^3/g$). Unlike the Fe-soc-MOF-1, the Fe exchanged by Cr led to full access of the pore volume similar to the parent Al analogue (FIG. 8). Exploration of oxygen and methane adsorption at 90 K and 112 K (FIGS. 15-16) confirmed the attainment of optimal porosity for the Cr-soc-MOF-1. Similar to the Al-soc-MOF-1 (current benchmark material for methane gravimetric uptake and delivery), $CH_4$ storage studies showed that Cr-soc-MOF-1 exhibited one of the highest $CH_4$ total volumetric and gravimetric uptakes (FIG. 17). Analysis of $CH_4$ sorption data showed that it exhibited a volumetric and gravimetric working capacity of 187.1 $cm^3/cm^3$ and 37.1 wt % respectively between 5-80 bar pressure range and at 298 K.

Water Adsorption Studies of Cr-soc-MOF-1

In order to develop a suitable porous material for water adsorption related applications, three criteria have been considered and targeted: (i) the pore filling or condensation of water into the pore system of the porous solid must exhibit a steep uptake isotherm at a specific relative humidity, depending on the nature of the targeted application, (ii) a high water uptake capacity for the requisite maximum delivery of water and a spontaneous adsorption-desorption processes for the desired energy efficiency and (iii) a highly reproducible cycling performance of the material towards water adsorption-desorption, an essential criteria for the prospective deployment in industrial application.

Figure 18A:
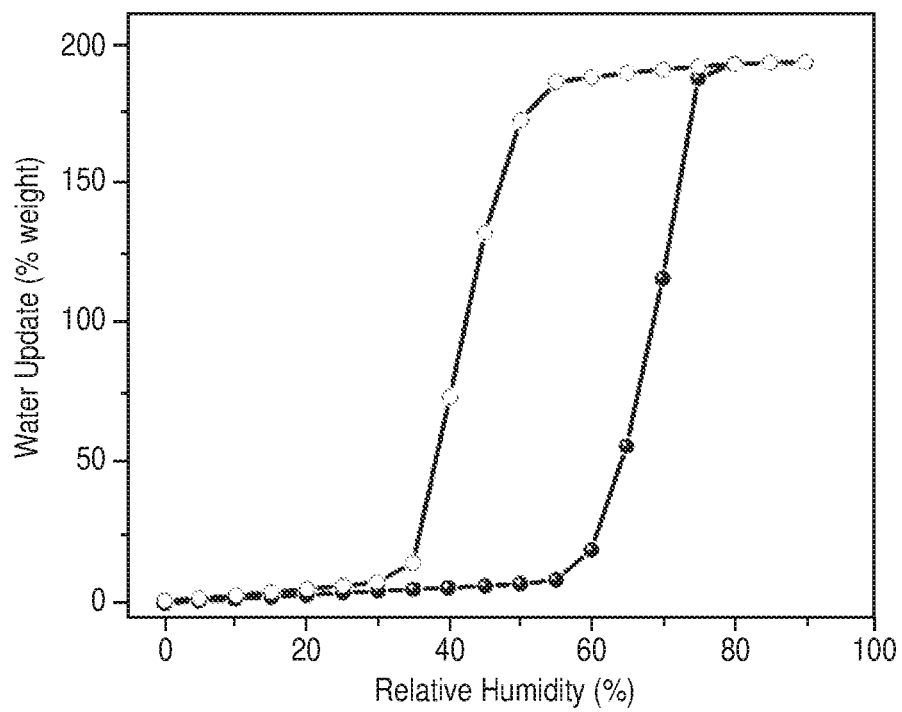
FIGS. 18A-18B are graphical views of (18A) water adsorption (solid spheres) and desorption (empty circles) isotherms at 298K for activated Cr-soc-MOF-1 and (18B) 100 cycles of water uptake profile vs relative humidity of the Cr-soc-MOF-1 at 298 K, according to one or more embodiments of the present disclosure.
Figure 18B:
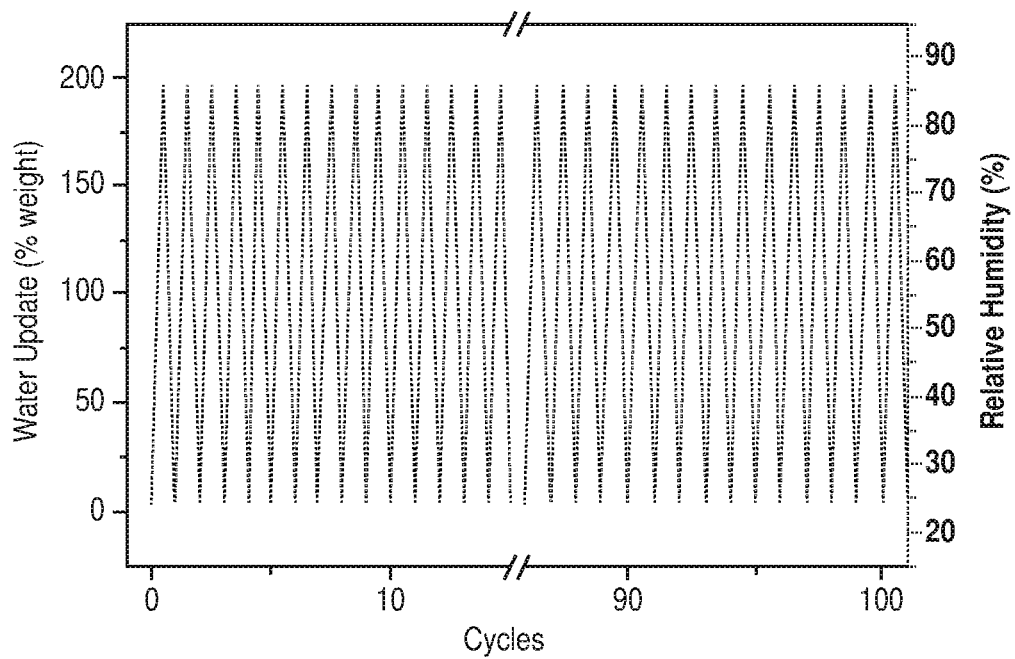

Based on these criteria and considering the combined exceptional porosity and the extremely high stability of the Cr-soc-MOF-1, water adsorption properties were extensively evaluated experimentally at ambient temperature (FIGS. 18A-18B). As depicted in the water adsorption isotherm (FIG. 18A), the adsorbed amount of water gradually increased with increasing the relative humidity (RH) up to about 55%, followed by a steep water uptake in the RH range between about 60% and about 75%. The Cr-soc-MOF-1 offered an exceptional maximum water uptake of 1.95 g (195 wt %) of adsorbed water per gram of sorbent at RH 75%, with an S shaped-like form of the adsorption isotherm.

To the best of present knowledge, this is the highest value of water adsorbed at saturation from all MOFs, carbons, and inorganic materials. The pore volume calculated from the water vapor adsorption at 298 K and at 0.95 $p/p_0$ (ca. 1.95 $cm^3/g$) was in excellent agreement with the calculated and experimental pore volume from nitrogen adsorption at 77 K, an unprecedented feature for MOFs with such high porosity and attested to the outstanding stability of Cr-soc-MOF-1 to water vapor. Interestingly, only one such example of high water cycling stability was reported for Cr-MIL-100-F, but with gradual uptake and much less water vapor total adsorption uptake (0.8 g/g vs 1.95 g/g for Cr-soc-MOF-1).

Figure 19:
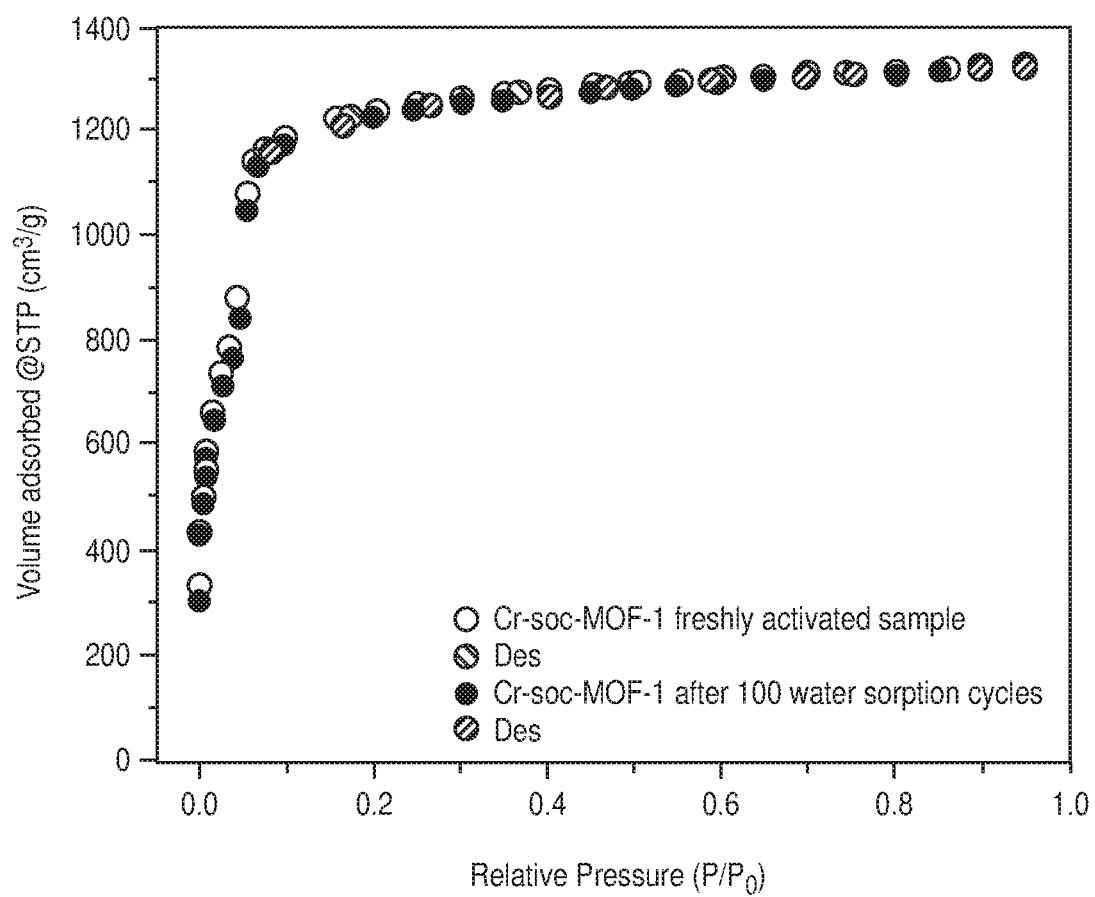
FIG. 19 is a nitrogen sorption isotherm at 77 K of freshly activated Cr-soc-MOF-1 and after 100 water adsorption-desorption cycles, according to one or more embodiments of the present disclosure.
Figure 20:
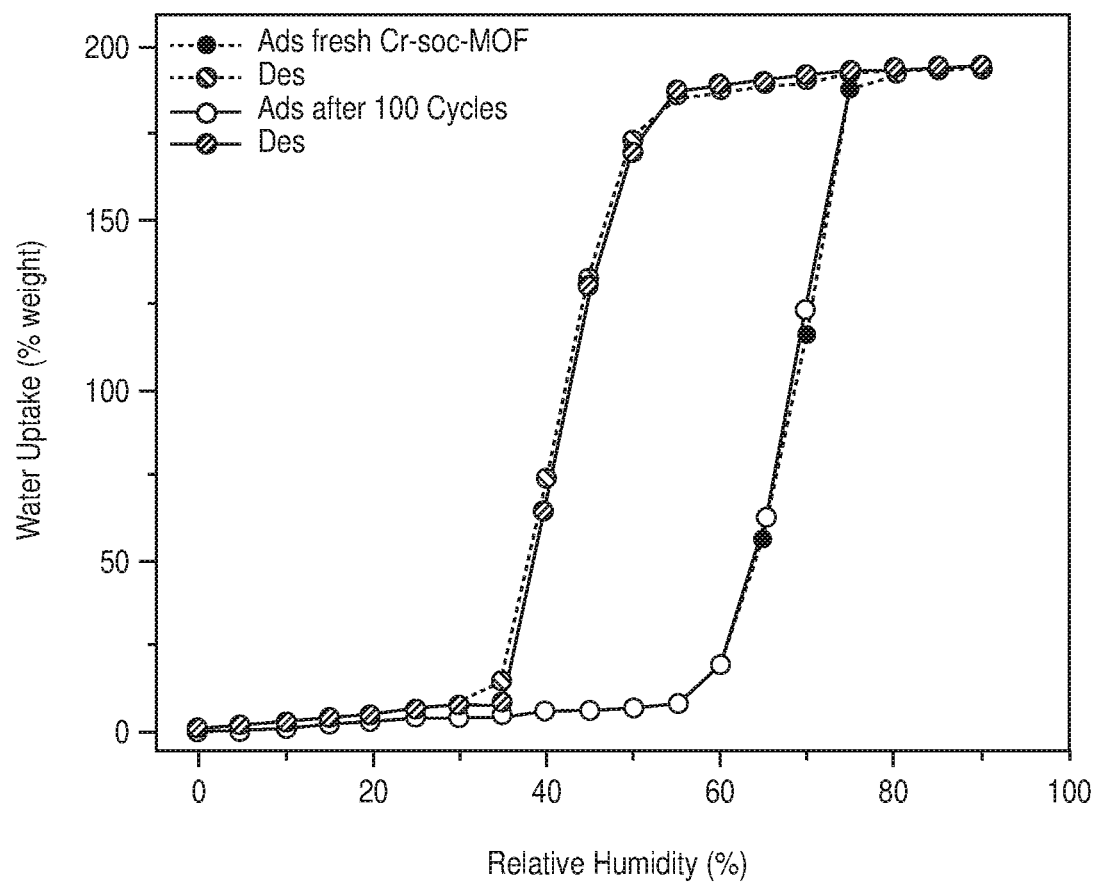
FIG. 20 is an overlay of water adsorption (solid spheres) and desorption (empty circles) isotherms at 298 K for activated fresh (in blue color) and after 100 water adsorption-desorption cycles (in red color) sample of Cr-soc-MOF-1, according to one or more embodiments of the present disclosure.

Markedly, the association of this extremely high water uptake with a distinct S shape water adsorption isotherm at 298K positioned Cr-soc-MOF-1 as a suitable adsorbent candidate for moisture control applications. Accordingly, the durability and recyclability of the Cr-soc-MOF-1 was evaluated by performing multiple water adsorption and desorption tests at 298 K, by simply altering the moisture levels between about RH 25% and about RH 85%. Delightfully, the water uptake remained unaltered throughout the hundred adsorption-/desorption cycles (FIG. 18B), performed between RH 25% and 85%, respectively. Considerately, the $N_2$ sorption isotherm and the water adsorption/desorption isotherms were collected on the sample after 100 water adsorption-desorption cycles and confirmed that the uptakes and the shape of the $N_2$ and water isotherms were preserved (FIGS. 19 and 120).

Figure 21:
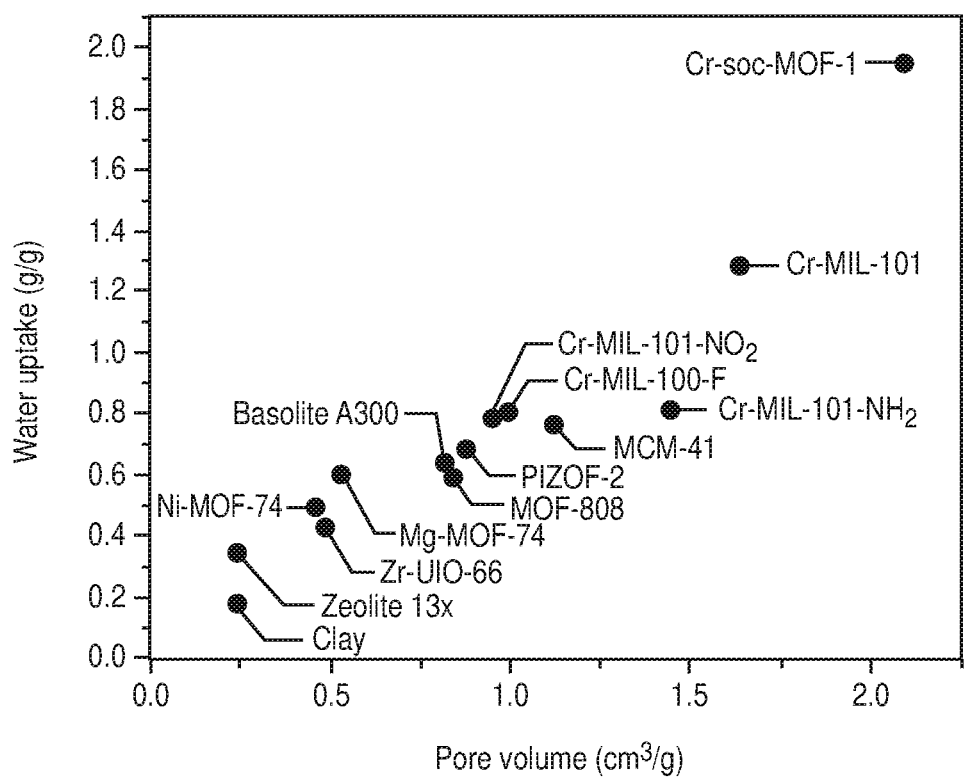
FIG. 21 is a graphical view of a correlation between pore volume and water uptake capacity for Cr-soc-MOF-1 as compared to conventional materials, according to one or more embodiments of the present disclosure.
Figure 22:
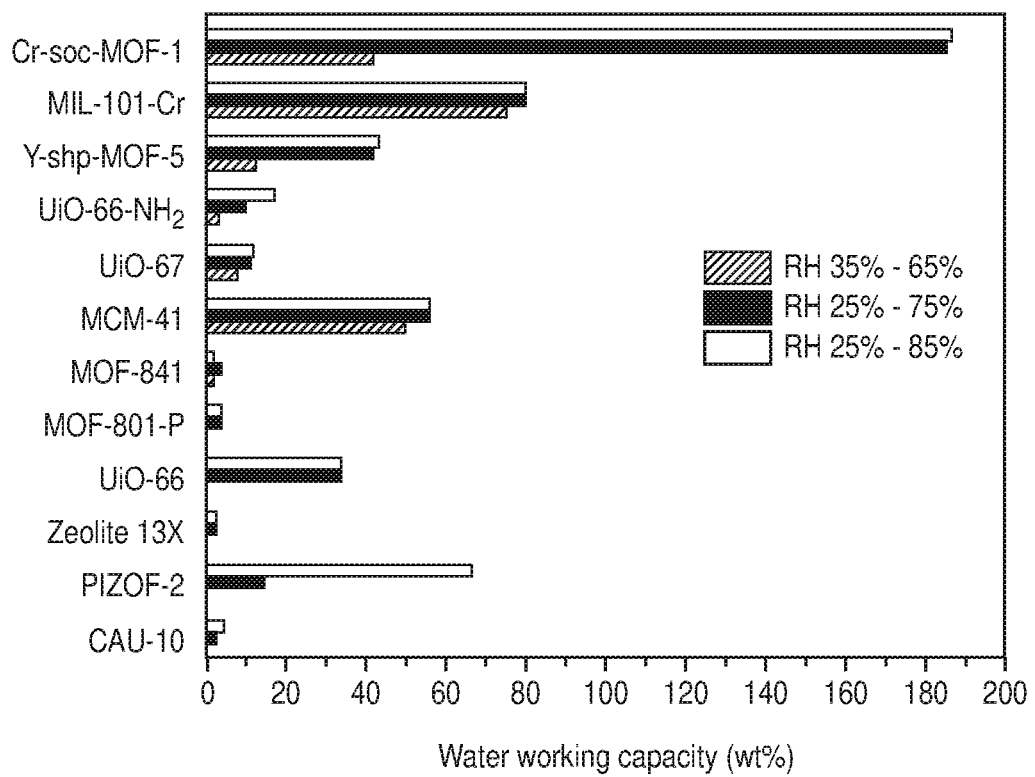
FIG. 22 is a graphical view illustrating working capacity at different relative humidity ranges (RH 35-65%, RH 25-75%, and RH 25-85%) relevant to indoor moisture control at room temperature, according to one or more embodiments of the present disclosure.

Further, the water adsorption performance of Cr-soc-MOF-1 was evaluated against the best performing existing materials for water adsorption and indoor moisture control application. Interestingly, the water uptake plotted for the best performing materials against their associated pore volume determined using nitrogen isotherm at 77 K (FIG. 21 and Table 4) showed that the Cr-soc-MOF-1 greatly outperformed all the materials reported to date in terms of total water adsorption capacity at ambient conditions. Noticeably, the pore volume determined from the water vapor adsorption isotherm for the Cr-soc-MOF-1 matched perfectly the corresponding pore volume derived theoretically from the crystal structure and experimentally using nitrogen adsorption isotherm (77 K). Manifestly, analysis of the water adsorption working capacity for different relative humidity ranges (RH 35-65%, RH 25-75% and 25-85% RH), relevant to indoor moisture control at room temperature, revealed that Cr-soc-MOF-1 outperformed all the materials reported so far for water adsorption (FIG. 22). Particularly, this comparative analysis showed that Cr-soc-MOF-1 displayed a 400% higher working uptake at room temperature than the current benchmark material, Y-shp-MOF-5, for moisture control in the RH 25-85% range.

Evidently, the Cr-soc-MOF-1's exceptional water adsorption features were a direct result of combining the requisite structural characteristics in a single adsorbent, namely hydrolytically stability, ultrahigh micropore volume and the proper pore system (shape, size and functionality), conferring the observed energy barrier during adsorption and desorption steps as reflected from the S-shaped adsorption isotherm at room temperature.

Figures 23A, 23B, 23C:
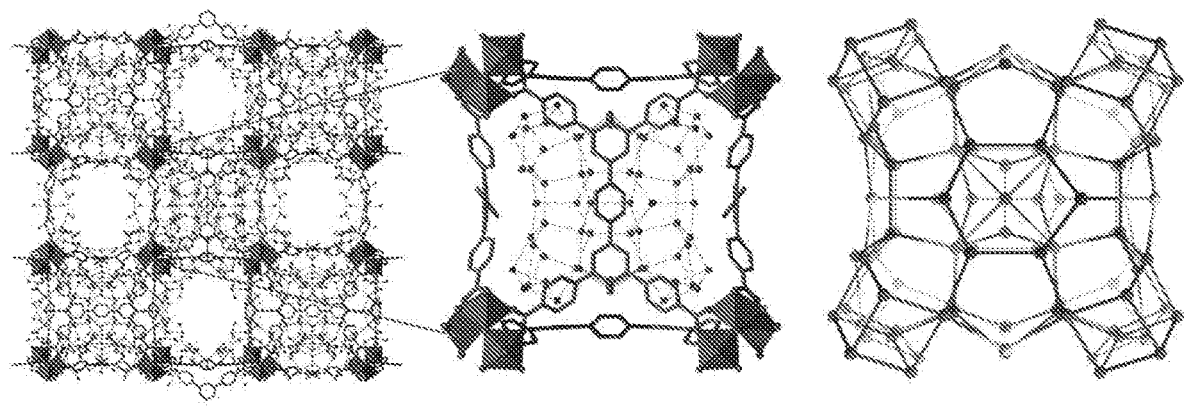
FIGS. 23A-23C are schematic diagrams of the crystal structure of hydrated Cr-soc-MOF-1, where (23A) is a packing diagram along the c axis with ahydrogen bonding network shown; (23B) is the ordered 114 water molecules cluster in the cubic cage; and (23C) is the cluster decomposition: water heptamers at the vertices of the cube (red), a single water molecule at the edges (yellow), hexamers at the faces (blue), incur cube (green), and a dimer (pink) (hydrogen atoms are omitted for clarity), according to one or more embodiments of the present disclosure.

In order to understand and gain better insights on the observed adsorption-desorption behavior, the crystal structure of the hydrated Cr-soc-MOF-1 (3) (Table 3) was further analyzed and appositely localized the guest water molecules within the MOF pore system (FIG. 23A). Distinctly, a closer examination of the adsorbed guest molecules revealed a significant disorder of the water molecules in the channels and a well-ordered 114 water molecules clusters within the cages (FIG. 23B), indicating the water adsorption was plausibly governed by the water molecules' nucleation within the pore system, corroborating the noted energy barrier during the adsorption step, followed by the formation of the observed large water clusters. The initial water adsorption was promoted by the formation of eight water heptamers, located at the vertices of the cubic cage (FIG. 23C, red), with O . . . . O distances in the range of 2.808(9)-2.829(8) Å and further connected by single water molecules at the edges (FIG. 23C, yellow) with hydrogen bonds of 2.709(8) and 2.803(9) Å. Additional adsorbed water molecules formed water hexamers (2.78(2)-2.84(1) Å) in a boat conformation, centered at each face of the cubic cages (FIG. 23C, blue), and were found to strongly interact with the heptamers (2.826(9) Å) than with the water molecule in edges (2.89(2) and 2.94(3) Å). The aforementioned 104 adsorbed water molecules (8×heptamer in the corner, 12×1 water in the edge, 6×hexamer in the face) constitute the first layer of the adsorbed water molecules within the cubic cage. The second adsorbed water layer encompassed eight additional water molecules, also arranged in cubic fashion (FIG. 23C, green), and bridged with neighboring hexamers (2.74(1) Å). The third 'water layer' consisted of a disordered water dimer (FIG. 23C, pink), where the interaction between the two water molecules was relatively stronger than with the previous neighboring layer (2.79(2) vs 2.92(1) Å). The self-assembled water cluster, consisting of 114 water molecules sustained by hydrogen bonds, was further expanded via additional hydrogen bonds with the other adsorbed water molecules within the channels through the shared cage/channel windows.

Notably, the presence of a well-defined water assembly/network within the Cr-soc-MOF-1 pore system supported the remarkable distinctive water adsorption/desorption properties, as reflected by the noticeably open hysteresis indicating the water desorption process entailed the need to surmount the energy barrier required for the dissociation of the hosted water hydrogen-bonded network. Significantly, the relatively higher energy of dissociation during the water desorption step inflicted the observed shift of the water desorption branch to a relatively lower pressures, a unique behavior not common for microporous materials. Evidently, the associated energy barriers to both the water adsorption/desorption steps on the Cr-soc-MOF-1 afforded the resultant interesting S-shaped like adsorption/desorption isotherms as recently observed with the Y-shp-MOF-5 adsorbent.

In summary, the first Cr-MOF was successfully synthesized with the underlying soc topology. Cr-soc-MOF-1, via post-synthetic modification approach. The resultant Cr-soc-MOF-1 exhibited a rare combination of high porosity, high thermal/chemical stability and high water vapor adsorption capacity. It preserved its optimal porosity even after being soaked in liquid water, a feature rarely observed for highly microporous MOFs, with an apparent surface area and pore volume close to 5000 $m^2/g$ and 2.1 $cm^3/g$. Furthermore, Cr-soc-MOF-1 was hydrolytically stable MOF with an unprecedented water loading/uptake (1.95 g/g) when compared to other MOFs reported so far. To the best of present knowledge, the reported Cr-soc-MOF-1 outperformed all existing MOFs in terms of total and working capacity, reversibility and cyclic performances particularly for indoor moisture control. The occurrence of S-shaped water adsorption/desorption isotherms was mainly governed by the formation and dissociation of water clusters during the adsorption and desorption steps, respectively. Another salient feature of that Cr-soc-MOF-1 was that the adsorbed water molecules were completely desorbed at room temperature just by simply reducing the relative humidity with no heating required, suggesting an energy-efficient and cost-effective recycling process. Practically, this newly constructed Cr-soc-MOF-1 met the required criteria for its conceivable deployment in real application such as water vapor removal in enclosed and confined spaces and dehumidification.

Single Crystal X-Ray Data

The crystal structures of $[Fe_3(\mu_3\text{-}O)(H_2O)_2(TCPT)_{1.5}Cl]$ (1) and $[Cr_3(\mu_3\ O)(H_2O)_2(TCPT)_{1.5}Cl]$ (2) were isostructural with Al-soc-MOF-1 (space group Pm-3n). In the series of $Fe^{3+}$, $Cr^{3+}$ and $Al^{3+}$ the cationic radii decreased, whereas the unit cell volume of the corresponding soc-MOF's increased. The reason was that the organic ligand molecule bended and was disordered over two positions. In the case of the hydrated Cr-soc-MOF-1 $[Cr_3(\mu_3\text{-}O)(H_2O)_2(TCPT)_{1.5}Cl]\cdot118.31(H_2O)$ (3), the framework was isoreticular but the crystal structure symmetry belonged to the space group Pm-3. The crystal of 3 was refined as a 2-component perfect merohedral twin which emulated Pm-3n. Due to the lower symmetry, there were two crystallographically independent organic ligand molecules. One of them revealed the same kind of disorder as in both 1 and 2, whereas the second one was ordered. Trials to apply the same space group and twin law as for 3 to the crystal structures of 1 and 2 did not improve the solutions, probably due to poor diffraction.

Due to significant disorder and poor diffraction, the geometry of the organic ligand was restrained to be reasonable with a set of DFIX and FLAT. Carbon atoms of the benzene rings were constrained by AFIX 66. Thermal parameters of all C atoms were restrained with strong RIGU command. Occupancies of C atoms were fixed at 0.5. Hydrogen atoms are placed at calculated positions and refined using a riding model with $U_{iso}(H)=1.2\ U_{eq}(C)$. Cl$^-$ anion and O1w atoms were refined with the same coordinates and $U_{ij}$ parameters. Strongly delocalized electron density was found in the voids of 1 and 2 and omitted from the refinement using the PLATON's SQUEEZE procedure. The pore volumes equal to 33489 and 32306 Å$^3$ for Fe-soc-MOF-1 and Cr-soc-MOF-1 (72.5 and 71.6% and 71.2% of the unit cell volume), respectively.

The PLATON's SQUEEZE procedure was also used for estimation of water amount included in 3. It was possible to localize 63.2% of water molecules (598.4 of 946.4 per unit cell) mainly in the cavities and also close to the windows to the channels. The contribution to the structure factors of strongly disordered electron density in the channels was excluded using the SQUEEZE.

TABLE 1

Crystal Data and Structure Refinement for Fe-soc-MOF-1 (1)

| | |
|---|---|
| Empirical formula | C$_{69}$H$_{43}$ClFe$_3$O$_{15}$ |
| Formula weight | 1315.03 |
| Crystal system, space group | Cubic, Pm-3n |
| Unit cell dimensions | a = 35.875 (2) Å |
| Volume | 46171(7)Å$^3$ |
| Z, calculated density | 8, 0.378 Mg m$^{-3}$ |
| F(000) | 5376 |
| Temperature (K) | 100.0(1) |
| Radiation type | Cu Kα |
| Absorption coefficient | 1.75 mm$^{-1}$ |
| Absorption correction | Multi-scan |
| Max and min transmission | 0.051 and 0.122 |
| Crystal size | 0.05 × 0.05 × 0.05 mm |
| Shape, color | Cube, yellow |
| θ range for data collection | 4.3-37.4° |
| Limiting indices | −28 ≤ h ≤ 14, −24 ≤ k ≤ 22, −5 ≤ l ≤ 29 |
| Reflection collected/unique/observed with I > 2σ(I) | 17519/2495 (R$_{int}$ = 0.088)/1653 |
| Completeness to θ$_{max}$ = 40.0° | 99.4% |
| Refinement method | Full-matrix least-squares on F$^2$ |
| Data/restraints/parameters | 2495/254/235 |
| Final R indices [I > 2σ(I)] | R$_1$ = 0.114, wR$_2$ = 0.351 |
| Final R indices (all data) | R$_1$ = 0.143, wR$_2$ = 0.372 |
| Weighting scheme | [σ$^2$(F$_o^2$) + (0.2P)$^2$]$^{-1}$* |
| Goodness-of-fit | 1.39 |
| Largest diff. peak and hole | 0.23 and −0.40 e Å$^{-3}$ |

TABLE 2

Crystal Data and Structure Refinement for Cr-soc-MOF-1 (2)

| | |
|---|---|
| Empirical formula | C$_{69}$H$_{43}$ClCr$_3$O$_{15}$ |
| Formula weight | 1303.48 |
| Crystal system, space group | Cubic, Pm-3n |
| Unit cell dimensions | a = 35.672(2) Å |
| Volume | 45393(7) Å$^3$ |
| Z, calculated density | 8, 0.381 Mg m$^{-3}$ |
| F(000) | 5328 |
| Temperature (K) | 296.0(1) |
| Radiation type | Cu Kα |
| Absorption coefficient | 1.43 mm$^{-1}$ |
| Absorption correction | Multi-scan |
| Max and min transmission | 0.747 and 0.504 |
| Crystal size | 0.05 × 0.05 × 0.05 mm |
| Shape, color | Cube, green |
| θ range for data collection | 4.3-34.2° |
| Limiting indices | −26 ≤ h ≤ 5, −25 ≤ k ≤ 17, −14 ≤ l ≤ 13 |
| Reflection collected/unique/observed with I > 2σ(I) | 14217/1666 (R$_{int}$ = 0.049)/1241 |
| Completeness to θmax = 34.2° | 99.4% |
| Refinement method | Full-matrix least-squares on F$^2$ |
| Data/restraints/parameters | 1666/306/223 |
| Final R indices [I > 2σ(I)] | R$_1$ = 0.142, wR$_2$ = 0.413 |
| Final R indices (all data) | R$_1$ = 0.162, wR$_2$ = 0.430 |
| Weighting scheme | [σ$^2$(F$_o^2$) + (0.2P)$^2$]$^{-1}$* |
| Goodness-of-fit | 1.91 |
| Largest diff. peak and hole | 0.42 and −0.40 e Å$^{-3}$ |

TABLE 3

Crystal Data and Structure Refinement for Cr-soc-MOF-1 · 118.3(H$_2$O) (3)

| | |
|---|---|
| Empirical formula | C$_{69}$H$_{279.62}$ClCr$_3$O$_{133.31}$ |
| Formula weight | 3434.99 |
| Crystal system, space group | Cubic, Pm-3 |
| Unit cell dimensions | a = 35.8199(4) Å |
| Volume | 45959(2) Å$^3$ |
| Z, calculated density | 8, 0.993 Mg m$^{-3}$ |
| F(000) | 14793 |
| Temperature (K) | 100.0(1) |
| Radiation type | Cu Kα |
| Absorption coefficient | 2.04 mm$^{-1}$ |
| Absorption correction | Multi-scan |
| Max and min transmission | 0.145 and 0.048 |
| Crystal size | 0.05 × 0.05 × 0.05 mm |
| Shape, color | Cube, green |
| θ range for data collection | 2.1-63.7° |
| Limiting indices | −23 ≤ h ≤ 38, −41 ≤ k ≤ 31, −37 ≤ l ≤ 39 |
| Reflection collected/unique/observed with I > 2σ(I) | 73308/13231 (R$_{int}$ = 0.056)/9080 |
| Completeness to θmax = 63.7° | 99.9% |
| Refinement method | Full-matrix least-squares on F$^2$ |
| Data/restraints/parameters | 13231/700/726 |
| Final R indices [I > 2σ(I)] | R$_1$ = 0.121, wR$_2$ = 0.313 |
| Final R indices (all data) | R$_1$ = 0.157, wR$_2$ = 0.345 |
| Weighting scheme | [σ$^2$(F$_o^2$) + (0.2P)$^2$]$^{-1}$* |
| Goodness-of-fit | 1.30 |
| Largest diff. peak and hole | 1.57 and −0.47 e Å$^{-3}$ |

TABLE 4

Pore volume and water uptake capacity for the best performing materials for water adsorption

| Material | Pore volume cm$^3$/g | Water uptake g/g | Reference |
|---|---|---|---|
| Cr-soc-MOF-1 | 2.1 | 1.95 | This work |
| Cr-MIL-101 | 1.64 | 1.29 | Ref. S7 [1] |
| Cr-MIL-101-NH$_2$ | 1.45 | 0.81 | Ref. S7 |
| Cr-MIL-100-F | 1 | 0.8 | Ref. S8 [2] |
| Mesoporous Silica MCM-41 | 1.12 | 0.76 | Ref. S9 [3] |
| Cr-MIL-101-NO$_2$ | 0.95 | 0.78 | Ref. S10 [4] |
| PIZOF-2 | 0.88 | 0.68 | Ref. S9 |
| Basolite A300 | 0.82 | 0.64 | Ref. S9 |
| MOF-808 | 0.84 | 0.59 | Ref. S9 |
| Zr-UiO-66 | 0.49 | 0.43 | Ref. S9 |
| Zeolite 13x | 0.24 | 0.34 | Ref. S9 |

TABLE 4-continued

Pore volume and water uptake capacity for the best performing materials for water adsorption

| Material | Pore volume cm³/g | Water uptake g/g | Reference |
|---|---|---|---|
| Clay (PTS-PILC) | 0.24 | 0.18 | Ref. S11 [5] |
| Ni-MOF-74 | 0.46 | 0.49 | Ref. S9 |
| Mg-MOF-74 | 0.53 | 0.6 | Ref. S9 |

[1] Ko, N., Choi, P. G., Hong, J., Yeo, M., Sung, S., Cordova, K. E., Park, H. J., Yang, J. K., and Kim, J. (2015). Tailoring the water adsorption properties of MIL-101 metal-organic frameworks by partial functionalization. J Mater Chem A 3, 2057-2064.
[2] George, A., Ryotaro, M., and Susumu, K. (2010). Highly Porous and Stable Coordination Polymers as Water Sorption Materials. Chemistry Letters 39, 360-361.
[3] Furukawa, H., Gándara, F., Zhang, Y.-B., Jiang, J., Queen, W. L., Hudson, M. R., and Yaghi, O. M. (2014). Water Adsorption in Porous Metal-Organic Frameworks and Related Materials. J Am Chem Soc 136, 4369-4381.
[4] Canivet, J., Bonnefoy, J., Daniel, C., Legrand, A., Coasne, B., and Farrusseng, D. (2014). Structure-property relationships of water adsorption in metal-organic frameworks. New J Chem 38, 3102-3111.
[5] S13. Pires, J., Pinto, M. L., Carvalho, A., and de Carvalho, M. B. (2003). Assesssment of Hydrophobic-Hydrophilic Properties of Microporous Materials from Water Adsorption Isotherms. Adsorption 9, 303-309.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

What is claimed is:

1. A method of sorbing water vapor, comprising:
    exposing a Cr-soc-MOF to an environment; and
    sorbing water vapor using the Cr-soc-MOF, wherein the Cr-soc-MOF adsorbs water vapor as a relative humidity of the environment increases.

2. The method of claim 1, wherein the Cr-soc-MOF desorbs water vapor as a relative humidity of the environment decreases.

3. The method of claim 1, wherein a working capacity of the Cr-soc-MOF is between about 35% RH and about 65% RH.

4. The method of claim 1, wherein a mass of adsorbed water is about two times a weight of the Cr-soc-MOF.

5. The method of claim 1, wherein a temperature of the environment is about room temperature.

6. The method of claim 1, wherein adsorbed water vapor is nearly completely desorbed by reducing relative humidity to about 25% RH.

7. The method of claim 1, wherein adsorbed water vapor is nearly completely desorbed by reducing relative humidity without heating and/or applying evacuation.

8. The method of claim 1, wherein the Cr-soc-MOF is stable over at least about 100 adsorption/desorption cycles.

9. The method of claim 1, wherein the environment is a confined or nearly confined space.

10. A method of making a metal-organic framework (MOF), comprising:
    contacting a template MOF of formula Fe-soc-MOF and a reactant including chromium in a presence of dimethylformamide (DMF) sufficient to replace Fe with Cr and form an exchanged MOF of formula Cr-soc-MOF.

11. The method of claim 10, wherein the exchanged MOF is one or more of isostructural and isoreticular with the template MOF.

12. The method of claim 10, wherein the exchanged MOF includes at least about 90% of chromium.

* * * * *